(12) United States Patent
Al Assad et al.

(10) Patent No.: US 9,247,920 B2
(45) Date of Patent: Feb. 2, 2016

(54) SYSTEM AND METHOD FOR PERFORMING BI-PLANE TOMOGRAPHIC ACQUISITIONS

(71) Applicant: GENERAL ELECTRIC COMPANY, Schenectady, NY (US)

(72) Inventors: Omar Al Assad, Niskayuna, NY (US); David Allen Langan, Clifton Park, NY (US); Bernhard Erich Hermann Claus, Niskayuna, NY (US); Jeffrey Wayne Eberhard, Albany, NY (US); Michel Francois Grimaud, Buc (FR)

(73) Assignee: General Electric Company, Niskayuna, NY (US)

( * ) Notice: Subject to any disclaimer, the term of this patent is extended or adjusted under 35 U.S.C. 154(b) by 74 days.

(21) Appl. No.: 14/192,466

(22) Filed: Feb. 27, 2014

(65) Prior Publication Data
US 2015/0238159 A1   Aug. 27, 2015

(51) Int. Cl.
A61B 6/00 (2006.01)
A61B 6/02 (2006.01)

(52) U.S. Cl.
CPC ............ *A61B 6/5258* (2013.01); *A61B 6/025* (2013.01); *A61B 6/4014* (2013.01); *A61B 6/4441* (2013.01); *A61B 6/482* (2013.01)

(58) Field of Classification Search
CPC .. A61B 6/4441; A61B 6/4014; A61B 6/4458; A61B 6/4464; A61B 6/032; A61B 6/481; A61B 6/504; A61B 6/4417; A61B 6/025; A61B 6/027; A61B 6/4007; A61B 6/4021; A61B 6/4035; A61B 6/4064; A61B 6/4291; A61B 6/466; A61B 6/484; A61B 6/503; A61B 8/0883; A61B 19/54; A61B 2019/5251; A61B 2019/5263; A61B 5/0422; A61B 5/7207; A61B 5/7289; A61B 6/482; A61B 6/5258
USPC ................... 378/8, 9, 21, 36, 62, 92, 82, 197
See application file for complete search history.

(56) References Cited

U.S. PATENT DOCUMENTS

| 4,577,222 A | 3/1986 | Kruger et al. |
| 5,226,066 A | 7/1993 | Barr |

(Continued)

FOREIGN PATENT DOCUMENTS

| WO | WO2009040742 | 4/2009 |
| WO | WO2012127339 | 9/2012 |
| WO | WO2012174263 | 12/2012 |

OTHER PUBLICATIONS

"Allura Xper FD10/10 Fuctional description", Philips, pp. 1-32. Apr. 2008.

(Continued)

*Primary Examiner* — Irakli Kiknadze
(74) *Attorney, Agent, or Firm* — Melissa K. Dobson

(57) ABSTRACT

A method includes, in a bi-plane interventional imaging system, moving a first C-arm supporting a first X-ray source and a first X-ray detector about first and second axes while obtaining a plurality of first X-ray attenuation data sets relating to a subject of interest; moving a second C-arm, positioned crosswise with respect to the first C-arm and supporting a second X-ray source and a second X-ray detector, about the first axis while obtaining a plurality of second X-ray attenuation data sets relating to the subject of interest; and synchronizing the movement of the first and second C-arms to avoid collision therebetween.

25 Claims, 9 Drawing Sheets

(56) References Cited

U.S. PATENT DOCUMENTS

| | | |
|---|---|---|
| 5,515,416 A | 5/1996 | Siczek et al. |
| 6,097,788 A | 8/2000 | Berenstein et al. |
| 6,435,713 B1 | 8/2002 | Iizuka |
| 6,904,119 B2 | 6/2005 | Oikawa |
| 7,103,136 B2 | 9/2006 | Claus et al. |
| 7,123,682 B2 | 10/2006 | Kotian et al. |
| 7,218,702 B2 | 5/2007 | Mistretta et al. |
| 7,519,412 B2 | 4/2009 | Mistretta |
| 7,594,751 B2 | 9/2009 | Grebner et al. |
| 7,660,382 B2 | 2/2010 | Grass et al. |
| 7,852,984 B2 | 12/2010 | Zellerhoff |
| 7,899,151 B2 | 3/2011 | Boese et al. |
| 7,899,152 B2 | 3/2011 | Boese et al. |
| 7,916,828 B1 | 3/2011 | Khare et al. |
| 8,023,707 B2 | 9/2011 | Boese et al. |
| 8,054,941 B2 | 11/2011 | Boese et al. |
| 8,094,773 B2 | 1/2012 | Boese et al. |
| 8,111,893 B2 | 2/2012 | Chen et al. |
| 8,175,358 B2 | 5/2012 | Weese et al. |
| 8,175,359 B2 | 5/2012 | O'Halloran et al. |
| 8,189,735 B2 | 5/2012 | Khare et al. |
| 8,229,547 B2 | 7/2012 | Rauscher-Scheibe |
| 8,265,224 B2 | 9/2012 | Baumgart |
| 8,279,996 B2 | 10/2012 | Allmendinger et al. |
| 8,285,014 B2 | 10/2012 | Lauritsch et al. |
| 8,363,782 B2 | 1/2013 | Kargar et al. |
| 2008/0247503 A1 | 10/2008 | Lauritsch et al. |
| 2009/0028290 A1* | 1/2009 | Grebner et al. ............ 378/9 |
| 2009/0092308 A1 | 4/2009 | Deuerling-Zheng et al. |
| 2009/0207968 A1* | 8/2009 | Grass ............................ 378/9 |
| 2009/0252378 A1 | 10/2009 | Boese |
| 2009/0264753 A1 | 10/2009 | Von Schulthess et al. |
| 2010/0208971 A1 | 8/2010 | Neukirchen et al. |
| 2010/0246916 A1 | 9/2010 | Deuerling-Zheng et al. |
| 2011/0038517 A1 | 2/2011 | Mistretta et al. |
| 2011/0268245 A1 | 11/2011 | Eberhard |
| 2012/0041301 A1 | 2/2012 | Redel |
| 2012/0085934 A1* | 4/2012 | Marcelis et al. ........... 250/491.1 |
| 2012/0114217 A1 | 5/2012 | Mistretta et al. |
| 2012/0136243 A1 | 5/2012 | Boese et al. |
| 2012/0190967 A1 | 7/2012 | Nahm |
| 2012/0300903 A1 | 11/2012 | Yao et al. |
| 2012/0328077 A1 | 12/2012 | Bouvier |
| 2013/0046176 A1 | 2/2013 | Mistretta et al. |

OTHER PUBLICATIONS

Siemens Axiom Innovations, "Artis zee Angiography", pp. 1-8, Nov. 2007.

Benson et al., "Chapter 2: Angiography", Percutaneous Interventions for Congenital Heart Disease, Sievert (ed.) pp. 15-31, Oct. 30, 2006.

"GE Healthcare Introduces Innova IGS 630 Biplane Interventional Imaging System", NeuroNews, Dec. 12, 2011, 1 page.

Bushberg et al., "Chapter 9: Fluoroscopy, Section 9.7, Fluoroscopy Suites", The Essential Physics of Medical Imaging 3rd Edition, pp. 301-303, Dec. 2011.

"Modular Devices Inc. introduces new Modular Lab with Bi-Plane X-Ray Imaging System", Modular Devices Inc, Apr. 30, 2008, online, 1 page.

Sadick et al., "Impact of Biplane Versus Single-Plane Imaging on Radiation Dose Contrast Load and Procedural Time in Coronary Angioplasty", British Journal of Radiology, pp. 379-393, vol. 83, May 2010.

"GE Healthcare Introduces Innova IGS 630 Biplane Interventional Imaging System", online, Nov. 29, 2011, pp. 1-2.

U.S. Appl. No. 14/090,677, filed Nov. 26, 2013, Khare et al.

* cited by examiner

SYSTEM AND METHOD FOR PERFORMING BI-PLANE TOMOGRAPHIC ACQUISITIONS

BACKGROUND

The subject matter disclosed herein relates to tomographic imaging and, more particularly, to performing tomographic imaging using data generated from two imaging planes.

Imaging technologies allow images of the internal structures of a patient or object to be obtained, thereby minimizing the invasive procedure on the patient or object. In particular, technologies such as X-ray fluoroscopy, X-ray computed tomography (CT), and tomosynthesis use various physical principles, such as the varying transmission of X-rays through a target volume, to acquire projection data and to construct images (e.g., three-dimensional, volumetric representations of the interior of the human body or of other imaged structures). However, various physical limitations or constraints on acquisition may result in artifacts or other imperfections in the reconstructed image. Furthermore, the bulk of certain systems, such as X-ray computed tomography systems, can preclude their use in conjunction with medical procedures, such as interventional procedures.

With respect to the resultant images obtained by certain X-ray systems, imaging methods that utilize X-ray projection images may suffer from artifacts due to incompleteness of the scan data. Truncation of data in certain directions (e.g., in the direction corresponding to the one or more axes about which the X-ray source rotates about the patient), mishandled data, and/or missing projection angles can often lead to such artifacts and imperfections. In addition, obtaining complete data sets can be time-consuming. Furthermore, it may be desirable to reduce the patient's exposure to X-rays.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a medical imaging system includes a first X-ray imager comprising: a first structure supporting a first X-ray source and a first X-ray detector, wherein the first structure is configured to move the first X-ray source and the first X-ray detector about an imaged volume; a second X-ray imager positioned crosswise relative to the first X-ray imager, comprising: a second structure supporting a second X-ray source and a second X-ray detector; and an imaging control system comprising one or more tangible, non-transitory, machine-readable media collectively storing one or more sets of instructions executable by one or more processors to: move the first X-ray source along a first trajectory about the imaged volume while obtaining first X-ray attenuation data of the imaged volume via a first acquisition, wherein the first trajectory is non-linear and is represented by a first path traced by a line connecting the first X-ray source and an iso-center of the imaged volume as the first X-ray source moves about the imaged volume from a start of the first acquisition to an end of the first acquisition; obtain second X-ray attenuation data of the imaged volume using the second X-ray source and the second X-ray detector; and synthesize a volumetric image from the first X-ray attenuation data using tomosynthesis and the second X-ray attenuation data.

In another embodiment, a method includes, in a bi-plane tomographic imaging system, moving a first X-ray source and a first X-ray detector about first and second axes to generate a first trajectory while obtaining a plurality of first X-ray attenuation data sets from an imaged volume via a first acquisition, wherein first trajectory is represented by a non-linear path traced by a line connecting the first X-ray source with an iso-center of the imaged volume as the first X-ray source moves about the imaged volume from a first time point of the first acquisition to a second time point of the first acquisition; obtaining a second X-ray attenuation data set from an imaged volume via a second acquisition using a second X-ray source and a second X-ray detector positioned crosswise with respect to the first X-ray source and the first X-ray detector; and synthesizing a volumetric image using at least one of the plurality of first X-ray attenuation data sets and the second X-ray attenuation data set as source data.

In a further embodiment, a system includes a medical imaging system, a first X-ray imager comprising: a first structure supporting a first X-ray source and a first X-ray detector, wherein the first structure is configured to move the first X-ray source and the first X-ray detector about an imaged volume; a second X-ray imager positioned crosswise relative to the first X-ray imager, comprising: a second structure supporting a second X-ray source and a second X-ray detector; and an imaging control system comprising one or more tangible, non-transitory, machine-readable media collectively storing one or more sets of instructions executable by one or more processors to: move the first X-ray source along a first trajectory about the imaged volume while obtaining first X-ray attenuation data of the imaged volume, wherein the first trajectory is linear and is represented by a first path traced by a line connecting the first X-ray source and an iso-center of the imaged volume as the first X-ray source moves about the imaged volume; obtain second X-ray attenuation data of the imaged volume using the second X-ray source and the second X-ray detector while maintaining the second X-ray source and the second X-ray detector in a single position; and synthesize a volumetric image from the first X-ray attenuation data using tomosynthesis and the second X-ray attenuation data.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
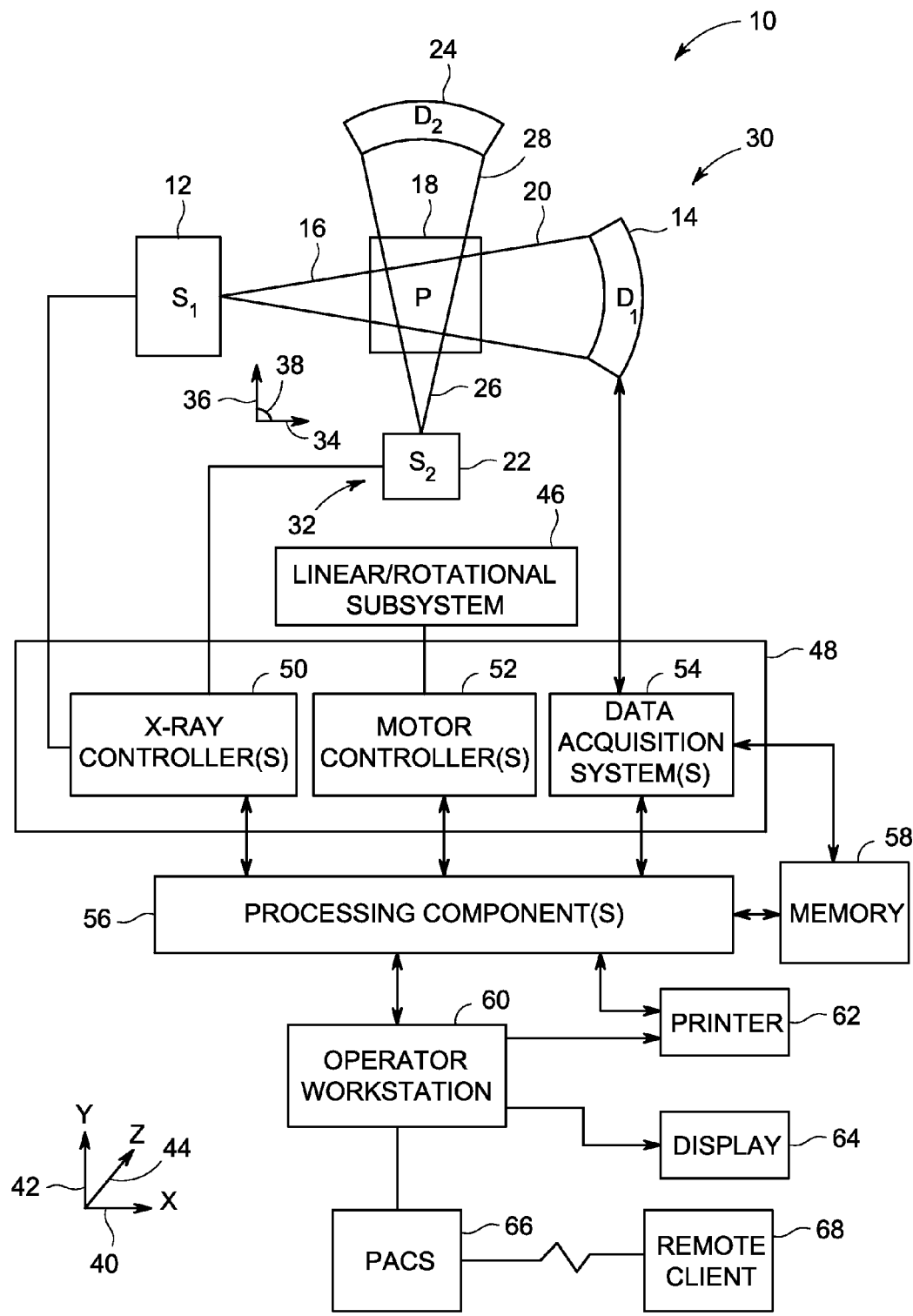
FIG. 1 is a diagrammatical view of an imaging system for use in producing images in accordance with aspects of the present disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The approaches disclosed herein may be suitable for use with a range of tomographic reconstruction systems. The present disclosure will primarily discuss the present approaches in the context of a biplane imaging system. However, it should be understood that the following discussion may also be applicable to other tomographic systems utilizing one, two, three, or more imagers that each obtain images in one, two, three, or more planes.

It should be noted that several embodiments described below refer to various imaging geometries, trajectories of imaging features (e.g., X-ray sources and detectors), rotational axes and directions, imaging planes, and the like. With respect to imaging geometry, it may be useful to refer to the imaged volume (e.g., a volume within a patient or other subject of interest), and to conceptually define a single point at or near the center of the imaged volume as the iso-center. In some systems, the iso-center may define a common point that is at or near the intersection of one or more axes of rotation. In other systems, a more general definition may be applied (e.g., where the imaged volume is described as the intersection between cones that are circumscribed by the cone-beam imaging at a suitable set of different projection angles). Any specific X-ray projection direction may, therefore, be defined by specifying the direction of a line connecting the X-ray source and the iso-center. In particular, the projection direction may be specified as the location of a point where this line (the line between X-ray source and iso-center) intersects a sphere that has the iso-center at its center. In other words, any projection angle or projection direction can now be defined by the location of a point on a sphere having the iso-center as its center.

Relative to this sphere, an imaging plane may be defined as a set of projection directions that are located within a certain angular range relative to a reference direction. For example, the frontal imaging plane may be used to describe projection views within an angular range that is within, for example, 60 degrees of the PA (posterior/anterior) direction of the patient. Similarly, the lateral imaging plane may be described as the set of projection directions within an angular range that is within 60 degrees of the lateral/horizontal left/right projection direction. In some contexts, the terms frontal and lateral imaging plane are also associated with physical imagers, with their nominal resting positions associated with the PA direction, and the left/right projection direction, respectively.

A tomosynthesis trajectory of an imager may be described as a line on the sphere, or a more complex, general shape (e.g., a curve, an ellipse, a circle, a rectangle, a polygon, etc.). Generally, a linear trajectory may be achieved by using a single axis of motion (e.g., an axis of rotation) for moving the X-ray source (note that the associated detector is generally positioned essentially opposite to the source relative to iso-center, and may also move when the X-ray source moves). However, in other embodiments, depending on the orientation of the linear trajectory and the specific mechanical structure of the system, performing a motion corresponding to this linear trajectory may involve actuation about more than one axis. Achieving the more complex trajectories noted above (i.e., not linear) generally involves actuating more than one axis. In some embodiments, 2 axes may be sufficient to achieve the more complex trajectories, but other embodiments may involve actuation about more than 2 axes. Further, each trajectory may have portions that are linear (e.g., a first time period of a trajectory that is linear) and portions that are non-linear (e.g., a second time period where the trajectory is non-linear). The trajectory may be determined based on the total time from the beginning of data acquisition to the end of data acquisition. In this way, the path that the X-ray source/detector follows may vary over time in embodiments where the trajectory is linear during a first time period and non-linear during a second time period. The variation is not limited to linear vs. non-linear paths. For example, in a first time period of the trajectory, the X-ray source and/or detector may follow a first path (which may be linear or non-linear), and during a second time period of the trajectory, the X-ray source and/or detector may follow a second path (which may be linear or non-linear) that is different from the first.

With this in mind, the embodiments described herein may refer to specific motion axes that are meant as examples. It should be noted, however, that the same or similar trajectories may be achieved by using/actuating one or more alternative axes, and such embodiments are meant to be encompassed by the present disclosure.

Three-dimensional (3D) or volumetric imaging in some interventional suites use a CT-like circular rotation of the source and detector around the patient, over an angular range of approximately 200 degrees. Note that in the present context this so-called spin acquisition corresponds to a linear trajectory on the sphere, and is generally performed using a single axis of motion. This acquisition configuration provides reasonable image quality for a variety of applications, but has significant negative impact on workflow due to the intrusiveness of the scan. For example, it may be difficult and disruptive for an interventional procedure to be performed as the imager acquires data due to significant workspace constraints. Furthermore, the 200 degree angular range is generally only achievable when the lateral imager is moved out of the way, which takes time and is also otherwise disruptive to the clinical workflow. With the lateral imager in place, only significantly smaller angular ranges can be achieved for a spin acquisition, which limits the achievable 3D image quality and makes it impractical.

In accordance with embodiments of the present disclosure, tomosynthesis may be used in place of a traditional CT-like spin arrangement to provide volumetric images while also being less disruptive to the workflow. Generally, the present disclosure provides for the acquisition of tomosynthesis data with one X-ray imager (a first imager) using a 2-axis trajectory (e.g., more complex than a line on the sphere having the iso-center discussed above), and augmenting the data from the first X-ray imager with data collected with a second X-ray imager. The full data (from both the first and the second imagers) is then used to create a volumetric image. Example arrangements of two X-ray imagers are discussed in further detail below with respect to FIGS. 1 and 2.

The second imager may be stationary, may move in a linear trajectory, or may move in a more complex trajectory, or may move in a combination of these trajectories at different times. In some scenarios, the motion of the first imager may be limited by the physical presence of the second imager (e.g., its support structures). In these situations, the motion of the second imager may be coordinated (e.g., spatially and temporally) with the motion of the first imager to move the second imager out of the motion path of the first imager. In some instances, no data is collected by the second imager, or only during part of its trajectory; while in other instances data is collected throughout its trajectory. The movement of these two imagers may be coordinated (e.g., by an X-ray controller) such that they at least partially occupy the same space at different times over at least a portion of their respective trajectories.

In some configurations, a dynamic process (e.g., perfusion) is observed, and imaging is performed during this process (e.g., starting some time before the onset of the dynamic process to collect baseline data (e.g., pre-perfusion data). Here, the imagers may cycle through each tomo trajectory multiple times. The trajectory may be defined such that the orbit time (i.e., time for one pass through the trajectory) is adapted to the time scale of the observed process. For example, in perfusion imaging, a suitable orbit time may be 3 seconds or less. For higher quality baseline data, the data collected before the onset of the dynamic process (e.g., before the injection of contrast media) may include data from an orbit with a larger angular range, and an associated longer orbit time compared to the trajectories used during the dynamic process. In some configurations, the approach may be used to perform DSA-like imaging (digital subtraction angiography). In this case, projection images are acquired before the injection of contrast (this dataset is usually termed "mask images") and after the injection projection images are collected (once or during multiple passes of the trajectory) at essentially the same projection directions, thereby enabling subtraction of the projection images (removing the anatomical background and leaving only the contrast medium, maybe as a function of time) before feeding the images into the reconstruction. Note that this DSA-type imaging requires at least a subset of projection directions to be visited before and after the injection of contrast. Orbit times, tomographic angles, frame rates, etc., may also be adapted/modified during the imaging process. Such adaptations/modifications may be made, for example, in response to physiologic events (e.g., breathing), or other events (tool motion, injection of contrast, operator intervention, etc.).

The data collection rate (e.g., frame rate) on each imager is either constant (e.g., 30 frames per second (fps)), is adapted to the trajectory (e.g., fixed number of frames per unit angular change in view direction), or is adapted to observe a dynamic process, and so on. The data collection between the two imagers is either interleaved (suitable switching scheme between beamlines, adapted to the target frame rate for each imager, e.g., a b a b a b a b . . . for same frame rate, or a b b a b b a b b a b b if framerate b is twice the framerate of a etc.), or sequential, or some hybrid scheme is used.

In still further embodiments, data may be collected over a part of each orbit only. Note that orbit time, detector size and/or resolution, readout rate, as well as other parameters may be the same between the two imagers, or may be different. In addition, for each imager, the detector may be cleared of cross-scatter (e.g., by reading a so-called scrub frame to clear the detector of any remaining signal before the actual exposure window) prior to initiating an X-ray exposure. The X-ray technique may be adapted (in voltage (kV), current (mAs), filtration, etc.), or dual energy data (i.e., data at multiple voltage levels) may be collected. The detector may also be displaced (e.g., moving closer and farther away from the iso-center, or rotating it in-plane) in order to optimize the amount of anatomy that is covered by the imaging.

With the foregoing in mind, an example of a biplane imaging system 10 designed to acquire X-ray attenuation data at a variety of views around a patient and suitable for tomographic imaging is provided in FIG. 1. In the embodiment illustrated in FIG. 1, imaging system 10 includes a first source of X-ray radiation 12 and a first detector 14. The first X-ray source 12 may be an X-ray tube, a distributed X-ray source (such as a solid-state or thermionic X-ray source) or any other source of X-ray radiation suitable for the acquisition of medical or other images.

The X-rays 16 generated by the first source 12 pass into a region in which a patient 18, is positioned. In the depicted example, the X-rays 16 are collimated to be a cone-shaped beam, e.g., a cone-beam, which passes through the imaged volume. A portion of the X-ray radiation 20 passes through or around the patient 18 (or other subject of interest) and impacts a detector array, represented generally as the first detector 14. Detector elements of the first detector 14 produce electrical signals that represent the intensity of the incident X-rays 20. These signals are acquired and processed to reconstruct images of the features within the patient 18.

The bi-plane imaging system 10 also includes a second source 22 of X-ray radiation and a second detector 24, which, like the first detector 14, may include an array of detector elements. The second source 22 also generates X-rays 26, which may be collimated to form any suitable shape (e.g., a cone). The X-rays 26 are partially attenuated such that a portion 28 passes through the patient 18 and impacts the second detector 24. The second detector 24 generates electrical signals, which are acquired and processed to reconstruct images of the features within the patient 18.

As discussed in further detail below, the first source 12 and first detector 14 may be a part of a first imager 30. The first imager 30 may acquire X-ray images or X-ray projection data within an angular range of the AP direction of the patient 18 (e.g., at least linearly and, in some embodiments, non-linearly along a sphere having the iso-center of the imaged volume), thereby defining data in a first plane (e.g., a frontal plane of the patient 18). The second source 22 and the second detector 24 may be a part of a second imager 32. The second imager 32 may acquire data within an angular range of the lateral direction of the patient 18 (e.g., at least linearly and, in some embodiments, non-linearly along a sphere having the iso-center of the imaged volume), thereby defining data in a second plane (e.g., a lateral plane of the patient 18). A variety of configurations may be employed where the first and second imagers 30, 32 obtain data that may be used together to construct and/or update one or more three-dimensional images of the patient 18 (e.g., tissues of interest of the patient 18).

As depicted, the first imager 30 positions the first source 12 and the first detector 14, at rest, generally along a first direction 34, which may correspond to the AP direction of the patient 18 in certain embodiments. The second imager 32 positions the second source 22 and the second detector 24, at rest, generally along a second direction 36, which may correspond to the lateral direction of the patient 18 in certain embodiments. The first and second directions 34, 36 may be oriented at an angle 38 relative to one another. The angle 38 may be any angle that is suitable to enable the first and second imagers 30, 32 to perform the techniques described herein. Further, the angle 38 may be adjusted by various features of the system 10, such as various linear and rotational systems or, in other embodiments, by an operator. Generally, the angle 38 may be between 30 and 180 degrees, but it may be desirable in certain embodiments for the first and second imagers 30, 32 to be oriented crosswise relative to one another, such as between 30 and 90 degrees, or between 90 and 150 degrees. In one embodiment, the angle 38 is approximately 90 degrees.

In accordance with present embodiments, the first imager and the second imager 30, 32 may be moved relative to the patient or imaged object and relative to one another along one or more axes. For example, the first imager 30 may rotate about a first axis of rotation 40, a second axis of rotation 42, or a third axis of rotation 44, or any combination thereof, and the second imager 32 may rotate about any one or a combination of these axes as well. In one embodiment, the rotation of the first and second imagers 30, 32 may be coordinated, as discussed in detail below.

For example, the first source 12 and the first detector 14 may rotate (e.g., pivot) about the second and third axes of rotation 42, 44. In rotating about these axes, the first source 12 and the first detector 14 may trace a circular trajectory around the first axis of rotation 40 (e.g., may trace a non-linear shape, e.g., a circle, along a sphere having the iso-center of the imaged volume as its center). The second source 22 and the second detector 24 may rotate (e.g., pivot) about the second axis of rotation 42 in a manner where they trace an arcuate trajectory about the first axis of rotation 40 (e.g., may trace a line along the sphere). Thus the first imager 30 may be positioned or moved such that its first source 12 and first detector 14 perform a continuous trajectory where the source 12 and detector 14 return to their original position (e.g., their resting position) by way of a non-linear path, while the second imager 32 may be positioned or moved such that its second source 22 and second detector 24 perform a trajectory that is traced back and forth along the same path (e.g., a linear path). However, in other embodiments, the second imager 32 may also rotate about an additional axis such as the first axis of rotation 40 or the third axis of rotation 44, such that it also performs a continuous non-linear trajectory. Performing a continuous non-linear trajectory using at least the first imager 30 may be desirable in order to minimize the amount of missing data.

The movement of the first imager 30 and/or the second imager 32 may be initiated and/or controlled by one or more linear/rotational subsystems 46. The linear/rotational subsystems 46 may, in one embodiment, include a single unit that controls the movement of the first and second sources 12, 22 and the first and second detectors 14, 24. In other embodiments, the linear/rotational subsystems 46 may include entirely separate imaging apparatus, such that the first apparatus that controls the movement of the first source 12 and the first detector 14 of the first imager 30 and a second apparatus that controls the movement of the second source 22 and the second detector 24 of the second imaging apparatus 32 are entirely separate from one another. The linear/rotational subsystems 46, as discussed in further detail below, may include support structures, motors, gears, bearings, and the like, that enable the rotational and/or translational movement of the imagers 30, 32. In one embodiment, the linear/rotational subsystems 46 may include a first structural apparatus (e.g., a c-arm apparatus having rotational movement about at least two axes) supporting the first source and detector 12, 14, and a second structural apparatus (e.g., a c-arm apparatus) supporting the second source and detector 22, 24.

A system controller 48 may govern the linear/rotational subsystems 46 that initiate and/or control the movement of the first and second imagers 30, 32. The system controller 48 may also include features that control the timing of the activation of the first and second sources 12, 22, for example, to control the acquisition of x-ray attenuation data obtained during a particular imaging sequence. The system controller 48 may also execute various signal processing and filtration functions, such as for initial adjustment of dynamic ranges, interleaving of digital projection data, and so forth. Therefore, in general, the system controller 48 may be considered to command operation of the entire imaging system 10 to execute examination protocols such as the bi-plane tomographic imaging sequences described herein. It should be noted that, to facilitate discussion, reference is made below to the system controller 48 as being the unit that controls acquisitions, movements, and so forth, using the imagers. However, embodiments where the system controller 48 acts in conjunction with other control devices (e.g., other control circuitry local to the imagers or remote to the system 10) are also encompassed by the present disclosure.

In the present context, the system controller 48 also includes signal processing circuitry and various other circuitry that enables the system controller 48 to control the operation of the first and second imagers 30, 32 and the linear/rotational subsystems 46. In the illustrated embodiment, the circuitry may include an x-ray controller 50, which may correspond to one or more processing devices that include one or more tangible, non-transitory, machine readable media collectively storing one or more sets of instructions executable by one or more processors. The instructions stored on the media of the x-ray controller 50 may enable the first and second X-ray sources 12 and 22 to be timed so as to interleave the acquisition of X-ray attenuation data. Circuitry of the system controller 48 may also include one or more motor controllers 52. The motor controllers 52 may also include one or more tangible, non-transitory, machine readable media collectively storing one or more sets of instructions executable by one or more processors to control the activation of various components that are responsible for moving the first and second sources 12, 22 and the first and second detectors 14, 24. For example, the one or more sets of instructions may coordinate movement of the first and second imagers 30, 32 such that the imagers obtain data from different projection directions, maintain a desired degree of angular separation, and also for collision avoidance. In other words, the instructions may be executable in order to perform a particular trajectory for each of the first and second imagers 30, 32.

The system controller 48 is also illustrated as including one or more data acquisition systems 54. Generally, the first and second detectors 14, 24 may be coupled to the system controller 48, and more particularly to the data acquisition systems 54. The data acquisition systems 54 may receive data collected by read out electronics of the first and second detectors 14, 24, and in certain embodiments may process the data (e.g., by converting analog to digital signals or to perform other filtering, transformation, or similar operations).

It should be noted that the one or more tangible, non-transitory, machine-readable media and the processors that are configured to perform the instructions stored on this media may be shared between the various components of the system controller 48. For instance, as illustrated, the x-ray controller 50, the motor controller 52, and the data acquisition systems 54 may share one or more processing components 56 that are each specifically configured to cooperate with one or more memory devices 58 storing instructions that, when executed by the processing components 56, perform the image acquisition techniques described herein. Further, the processing components 56 and the memory components 58 may coordinate in order to perform various image reconstruction processes. For example, in one embodiment, the first imager 30 may obtain a set of X-ray attenuation data that is incomplete, but amenable to tomosynthesis. The set of data obtained by the first imager 30 may also have data that was obtained from an angularly-constrained trajectory, such that the data does not include data obtained from certain angular projection directions.

On the other hand, the second imager 32 may obtain projection images (e.g., one or more fluoroscopic images) and/or attenuation data from angular projection directions at which the first imager 30 is unable to be positioned. In this way, the second imager 32 may, in certain embodiments, generate data that can be combined with the data generated by the first imager 30 in order to provide additional data from additional projection directions, which can enhance image quality and reduce overall scan times. Furthermore, the processing components 56 and the memory components 58, as set forth herein, may be the components that are responsible for performing some or all of the any of the methods described below. These components are generally referred to as the system controller 48 to facilitate discussion.

The system controller 48 and the various circuitry that it includes, as well as the processing and memory components 56, 58, may be accessed or otherwise controlled by an operator via an operator workstation 60. The operator workstation 60 may include any application-specific or general-purpose computer that may include one or more programs (for example one or more imaging programs) capable of enabling operator input for the techniques described herein. The operator workstation 60 may include various input devices such as a mouse, a keyboard, a trackball, or any other similar feature that enables the operator to interact with the computer. The operator workstation 60 may enable the operator to control various imaging parameters, for example, by adjusting certain instructions stored on the memory devices 58 that cause the first and second imagers 30, 32 to perform different data acquisition sequences.

The operator workstation 60 may be communicatively coupled to a printer 62 for printing images, patient data, and the like. The operator workstation 60 may also be in communication with a display 64 that enables the operator to view various parameters in real time, to view images produced by the acquired data, and the like. The operator workstation 60 may also, in certain embodiments, be communicatively coupled to a picture archiving and communication system (PACS) 66. Such a system may enable the storage of patient data, patient images, image acquisition parameters, and the like. This stored information may be shared through imaging facility and may also be shared with other facilities, for example, a remote client 68. The remote client 68 may include hospitals, doctors' offices, or any other similar client.

Figure 2:
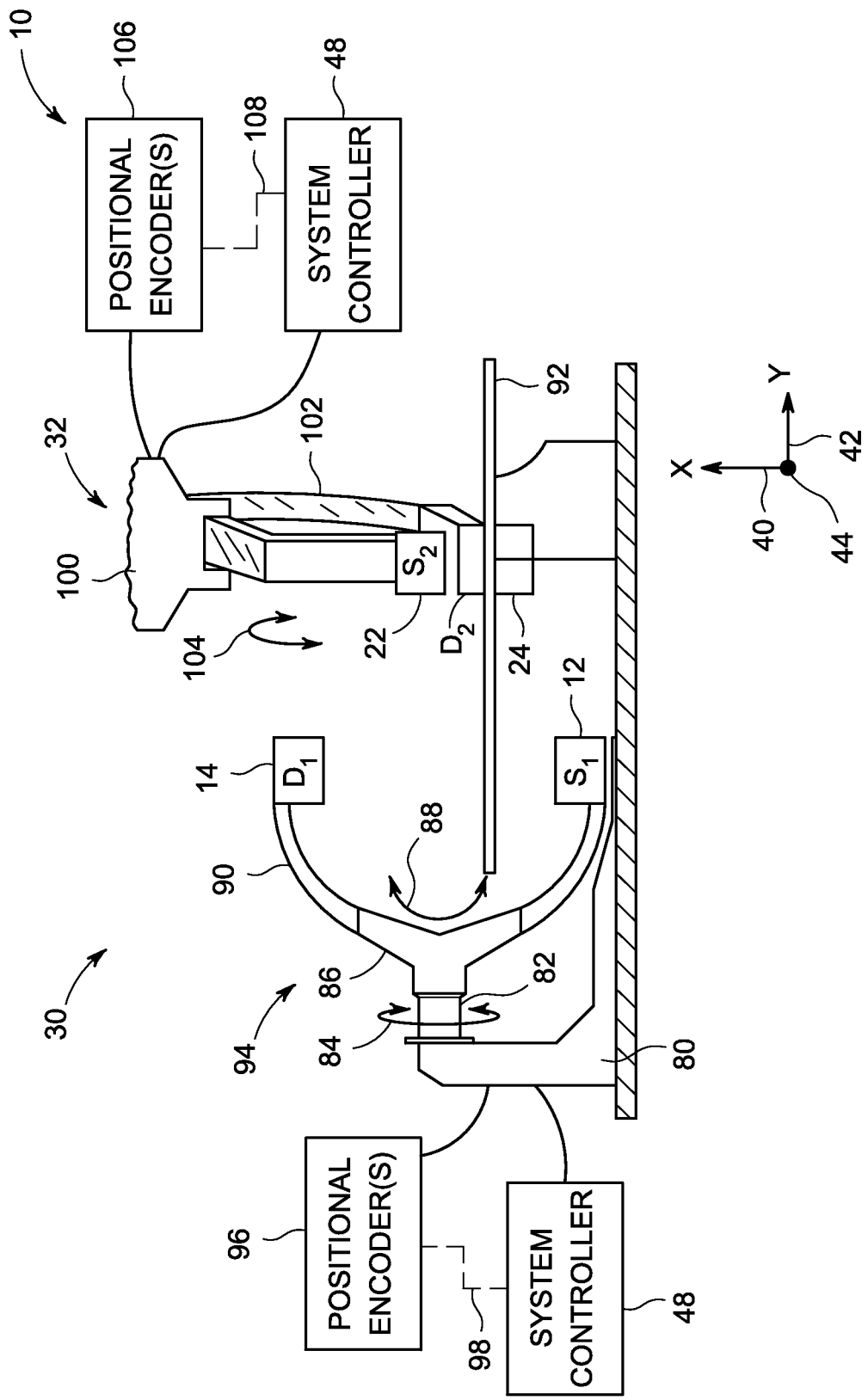
FIG. 2 is a schematic side view of a bi-plane imaging system in which a first imaging apparatus and a second imaging apparatus each obtain projection data along a plane, and the first imaging apparatus obtains projection data via rotation about two axes, in accordance with aspects of the present disclosure.

Various aspects of the present approaches may be further appreciated with respect to FIG. 2, which is a side view of an embodiment of the system 10. As illustrated, the system 10 includes the first imager 30 and the second imager 32. It should be noted that in practice, the second imager 32 may actually be closer in space to the first imager 30 than as illustrated in FIG. 2 (e.g., moved to the left in the illustration). However, to facilitate discussion of the present techniques and for clarity, the second imager 32 is depicted as being positioned further away from where it would, in practice, image the patient 18. The first imager 30, as illustrated, includes a first base 80 and a rotatable extension 82 extending from the first base 80. In the illustrated embodiment, the first base 80 is a floor-mounted base such that the first imager 30 may be secured to a floor of an imaging area in which it is positioned. In other embodiments, however, the first base 80 may not be secured to the floor (e.g., may be movable). The rotatable extension 82 is depicted as extending generally along the second axis of rotation 42, and enables the first source 12 and the first detector 14 to rotate about the second axis of rotation 42. For example, the rotatable extension 82 may enable the first source 12 and the first detector 14 to rotate about the second axis of rotation 42 in a manner that maintains their position relative to one another throughout the rotation. The rotation enabled by the rotatable extension 82 is shown as double-headed arrow 84, and may enable rotation relative to a median plane of the patient 18 from rest (e.g., generally aligned with the median plane of the patient 18), denoted as 0° (which also corresponds to the AP direction of the patient 18), up to between approximately 80° and 120° (e.g., in magnitude), such as at least 90° e.g., between approximately 90° and 110° (e.g., approximately 105°) in magnitude. The rotation may be in a clockwise or a counter-clockwise rotational direction, or both, in which case the angular displacement may be represented as a negative angular displacement in one direction and a positive angular displacement in the other. Thus, when rotating in one direction, the rotation may be at least 90°, e.g., between approximately 90° and 110° (e.g., approximately 105°) in the one direction, and at least −90°, e.g., between approximately −90° and −110° (e.g., approximately −115°) when rotating in the other direction. Indeed, all angles discussed herein are intended to include this relationship. It should be noted that the angular ranges discussed here relate to the range of motion for the first imager 30, when the range of motion is not limited by the presence of the second imager 32. When the second imager 32 is present, the angular ranges are correspondingly smaller, and may depend on the specific angulation of the second imager 32. With reference to the discussion above relating to trajectories, rotation about the second axis of rotation 42 may be considered to cause the first X-ray source 12 to trace a linear trajectory along the sphere having the iso-center of an imaged volume as its center.

The rotatable extension 82 is coupled to a first moving structure 86 (e.g., directly or indirectly via an extension arm), which enables the first source 12 and the first detector 14 to rotate about the third axis of rotation 44. This rotation about the third axis of rotation 44 is depicted as double-headed arrow 88, and may traverse a magnitude of angular displacement of between approximately 0 degrees (resting position) and 90 degrees, such as between approximately 10 degrees and 45 degrees at an orientation crosswise relative to the angular displacement caused by the rotatable extension 82. Therefore, rotation about the third axis of rotation 44 caused by the first moving structure 86 may be considered to trace another line along the sphere having the iso-center of the imaged volume, where this line is crosswise relative to the line created by the rotatable extension 82. These trajectories may be combined to generate non-linear, complex trajectories (e.g., ellipse, circle, rectangle, etc.).

By way of example, the first moving structure 86 may be a geared or track structure that is motively coupled to a first support structure 90 that physically supports the first source 12 and the first detector 14, and may be in the form of a c-arm, or any other shape that positions the first source 12 and the first detector 14 on either side of the patient 18. As illustrated, the first support structure 90 includes an arcuate structure that extends from a first side of a patient table 92, around the patient table 92, and to a second side of the patient table 92. In this way, the first source 12 and the first detector 14 generally remain positioned at opposite ends and/or on opposite sides of the patient table 92. Together, the first base 80, the rotatable extension 82, the first moving structure 86, and the first support structure 90 may be considered to be the first structure 94 of the first imager 30.

The first imager 30 may include various motors, actuators, or other features responsible for movement of the various structures of the first imager 30, and they may be communicatively coupled to one or more positional encoders 96. For example, the communicative coupling may be wireless or wired. The one or more positional encoders 96 may encode the respective positions of any one or more components of the first imager 30 in a manner that facilitates processing by the system controller 48. For example, the positional encoder 96 may encode the respective position of the first source 12, the first detector 14, the first support structure 90, the first moving structure 96, or any combination of these or other features of the first imager 30. The positional encoders 96 may provide feedback 98 (for example via wired or wireless signals) to the system controller 48. This feedback provided to the system controller 48 may enable the system 48 to determine the positions of the various components of the first imager 30 relative to various components of the second imager 32, relative to the space of the imaging area, relative to the table 92, or relative to any other appropriate reference. By way of example, the system controller 48 may generate, for example using various algorithms on the processing and memory devices discussed above, a space-time occupancy model that models the position of at least the first source 12 and the first detector 14 as a function of time based on imaging acquisition sequences, a time during acquisition sequence, the structural arrangement of the first imager 30, or the like. While the positional encoders 96 may generally be any device capable of generating feedback that may be processed by the system controller 48, the positional encoder 96 may include one or more antennas, RFID devices, electromagnetic devices, or the like. Again, the system controller 48 may use this feedback 98 to control either or both the first imager 30 and the second imager 32.

In the illustrated embodiment, the second imager 32 is depicted as including a second base 100. The second base 100 may be mounted to any structure, or may be a mobile base. However, in the illustrated embodiment, the second base 100 is depicted as a ceiling-mounted structure. The second base 100 may also include various motive devices such as gears, actuators, tracks, or any similar features that enable movement of the second source 22 and the second detector 24 as discussed below. Specifically, the second base 100 is physically and motively coupled to a second support structure 102, which is depicted as a curved structure that suspends the second source 22 and the second detector 24 on opposite sides or ends of the patient table 92 (e.g., along a lateral direction of the patient 18). The motive devices or similar features of the second imager 32 may operate to rotate the second source 22 and the second detector 24 about the patient table 92 in one or more rotational directions.

In one embodiment, the second source 22 and the second detector 24 may rotate about the second axis of rotation 42 or another axis of rotation that is crosswise relative to at least one of the axes of rotation of the first imager 30. The rotation by the second imager 32 is depicted as double-headed arrow 104, and may displace the second source and detector 22, 24 together by a magnitude of between 0 degrees and 90 degrees from its resting position, which is generally along the lateral direction of the patient 18, such as at least 5 degrees (e.g., between approximately 5 degrees and 15 degrees, or between approximately 10 degrees and 20 degrees). This trajectory may be represented as a linear trajectory that traces a line along the sphere having the iso-center of the imaged volume. In some embodiments, the data acquired with the second imager 32 is used as a partial set of data that is used to reconstruct a 3D volume. Furthermore, while the second imager 32 is depicted as rotating the second source 22 and the second detector 24 about the second axis of rotation 42 (e.g., only one axis), it should be noted that the second source 22 and the second detector 24 may be rotated about an additional axis of rotation, or may not be moved at all during the acquisition. For example, the second source 22 and the second detector 24 may be rotated about the first axis of rotation 40 or the third axis of rotation 44 in addition to being rotated about the second axis of rotation 42. Obtaining data along the additional trajectory traversed by the second imager 32 may be desirable to obtain data that can be useful in reconstructing three-dimensional images from incomplete data sets acquired using the first imager 30.

Like the first imager 30, the second imager 32 is depicted as being communicatively coupled (for example via wired or wireless communication) to one or more positional encoders 106, which may be shared with the first imager 30 or may be entirely separate from the first imager 30. The positional encoders 106 may encode the position of any one or more of the second base 100, the second support structure 102, the second detector 22 or the second detector 24, or any other feature of the second imager 32. The positional encoder 106 may provide feedback 108 to the system controller 48 to enable the system controller 48 to determine the position of the features of the second imager 32 relative to the features of the first imager 30, or relative to any other appropriate reference (e.g., a three-dimensional space established by one or more transmitting devices). For example, the system controller 48 may generate a space-time occupancy model for the second imager 32 that models the second source 22 and the second detector 24 as a function of a particular acquisition sequence as well as the current time during the given acquisition sequence. In this way, the system controller 48 may ascertain the respective positions of the first source 12, the first detector 14, the second source 22, and the second detector 24—both in the space of the established coordinate frame (e.g., established by a transmitter attached to the patient 18, the table 92, or the like), as well as relative to one another. Furthermore, the system controller 48 using one or more such models, may adjust one or more parameters of the models (e.g., before a procedure or during the procedure) and/or may adjust one or more acquisition parameters of either or both the first imager 30 and the second imager 32 in order to obtain data in a desired manner using the first imager 30 and the second imager 32. Example acquisitions are discussed in further detail below with respect to FIGS. 4-9.

As an example, the system controller 48 may simultaneously move the first source 12 and the first detector 14 together about the first axis of rotation 40, the second axis of rotation 42, or the third axis of rotation 44, or any combination thereof, in order to obtain first X-ray attenuation data. At substantially the same time, the system controller 48 may simultaneously move the second source 22 and the second detector 24 together about the first, second, or third axes of rotation 40, 42, 44, or any combination thereof, in order to obtain second X-ray attenuation data. The system controller 48 may receive positional information from the positional encoders 96, 106, relating to the first imager 30 and the second imager 32, and may calculate a trajectory (or update a modeled trajectory) for either or for both of the first source and detector 12, 14 and the second source and detector 22, 24 that avoids collision between the first and second imagers 30, 32 (e.g., by maintaining a desired angular separation between them).

Furthermore, the system controller 48 may synthesize one or more volumetric images using data obtained by the first imager 30 and the second imager 32. For example, in one embodiment, projection images/data obtained by the second imager 32 may be used to supplement the data obtained by the first imager 30 for reconstruction of a 3D image. In such an embodiment, the first imager 30 may perform a first acquisition of data using a first trajectory (e.g., a circular, ellipsoidal, or similar path traced by the first source 12 below the patient 18 and a corresponding circular, ellipsoidal, or similar path traced by the first detector above the patient 18, referred to herein as a frontal tomo trajectory). Thus, a trajectory generated by the first X-ray source 12 may be considered to trace such a path along the sphere having the iso-center. In this example, the first imager 30 may obtain projection data from a plurality of projection directions, but these projection directions may be limited by the angular range of motion of the first imager 30 (e.g., the limited angular displacement about the second rotational axis 42) and/or the presence of structures associated with the second imager 32, or other devices or structures. In accordance with certain embodiments, the second imager 32 may rotate about the second rotational axis 42 at projection directions beyond those obtained by the first imager 30 (e.g., at larger angles relative to the frontal plane of the patient 18). Thus, the data obtained by the second imager 32 may complement the data obtained by the first imager 30, and may enable the system controller 48 (or other reconstruction device) to perform tomosynthesis using a more complete set of data. This data may be considered to be obtained by the second imager 32 via lateral plane imaging, in that the second X-ray source 22 may generate a trajectory that may trace a line or non-linear path along the sphere having the iso-center from a position of rest approximating the lateral direction of the patient 18 (and at angular displacements therefrom). Various tomosynthesis algorithms that may be used include those that are well known by those of ordinary skill in the art, and may be of the analytical or iterative type, including but not limited to filtered back projection.

It should be noted that a variety of trajectories enabled by their respective rotational directions may be used for the first imager 30 and the second imager 32 in order to obtain a desired data set. Indeed, many combinations may be used such as, but not limited to, trajectories that are linear, and trajectories that are more complex, non-linear trajectories (e.g., circular, ellipsoidal, trapezoidal, triangular, square, rectangular, or any other shaped trajectory). As discussed above, the trajectory performed by the first imager 30 may be a tomographic trajectory where the first source 12 and the first detector 14 obtain frontal data relating to the patient 18 (e.g., attenuation data obtained across a first plane of the patient 18), and the trajectory performed by the second imager 32 may be a trajectory where the second source 22 and the second detector 24 obtain lateral data relating to the patient 18 (e.g., attenuation data obtained across a second plane of the patient 18 oriented crosswise (e.g., between 1 and 90 degrees) relative to the first plane of the patient 18).

In certain embodiments, data acquisition by the first and second imagers 30, 32 may be interleaved in order to avoid signal contamination between the imagers. Furthermore, in situations where both the first imager 30 and the second imager 32 obtain data using tomo trajectories, the sampling rate may not necessarily be the same for the first imager 30 and the second imager 32. For example, more data points obtained from one perspective may be acquired using the first imager 30 compared to the second imager 32, or vice-versa.

Figure 3:
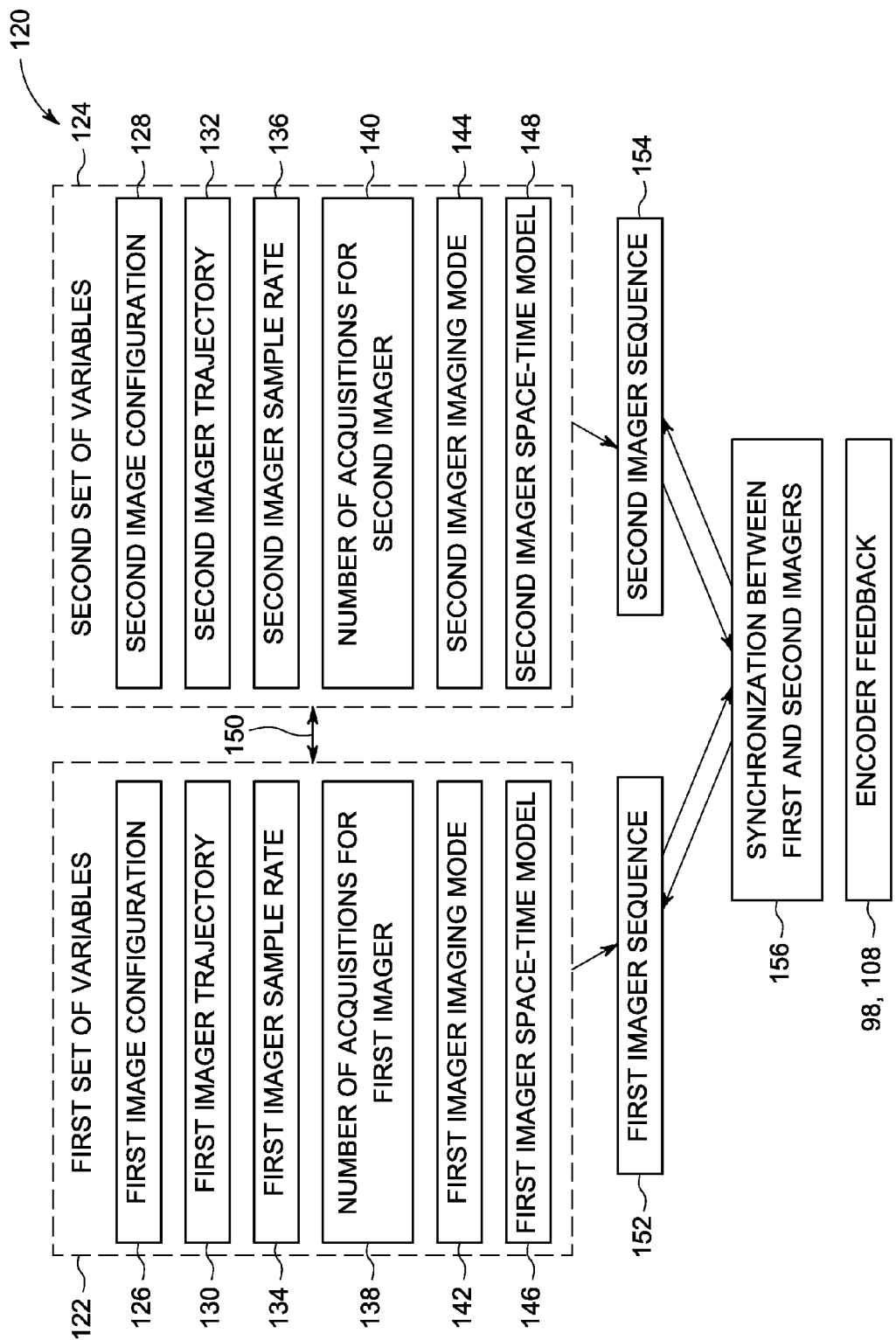
FIG. 3 is a diagram depicting a number of variables relating to the first and second imagers of FIGS. 1 and 2, which may be used to generate imaging sequences for the first and second imagers, in accordance with aspects of the present disclosure.

The various combinations of trajectories traced by the first and second imagers 30, 32 may be both space and time dependent, and therefore a space-time occupancy model either generated or used by the system controller 48 for both the first imager 30 and the second imager 32 may be useful in order to obtain two sets of desired data while also avoiding collisions, crosstalk, and the like, between both of the imagers. In this respect, the system controller 48 utilizes a number of variables in order to ultimately generate an imaging sequence for first imager 30 and the second imager 32. FIG. 3 presents an example scheme 120 of the manner in which a first set of variables 122 relating to the first imager 30 may be used in conjunction with a second set of variables 124 relating to the second imager 132 in order to generate their respective imaging sequences.

The first set of variables 122 includes a first imager configuration 126. The first imager configuration 126 may include input data to the system controller 48 relating to the shape of the first imager 30, the size of the first imager 30, and the relative positioning of various features of the first imager 30. For example, the first imager configuration 126 may include the relative positioning of the first source 12 and the first detector 14 as well as their space occupancy when supported by the first support structure 90, and when coupled to the first moving structure 86, the rotatable extension 82, and the first base 80. This data may be represented as a set of coordinates within an established coordinate frame that are occupied by the first imager 30 (e.g., the first source 12, the first detector 14).

Similarly, the second set of variables 124 may include a second imager configuration 128. The second imager configuration 128 may include size and shape information relating to the second imager 32, such as relative positioning of the second source 22 and the second detector 24, as well as the space occupancy of various features of the second imager of 32. For example, the second imager 128 may also include the space occupied by the second support structure 102 as well as the second base 100. The space occupancy data may be represented as a set of coordinates within the same established coordinate frame, a similar established coordinate frame, or an entirely separate coordinate frame, used for the first imager 30. The set of coordinates may represent coordinates that are occupied by the second imager 32 (e.g., the second source 22, the second detector 24).

The first and second sets of variables 122, 124 may also include a first imager trajectory 130 and a second imager trajectory 132, respectively. The first imager trajectory 130 may generally set forth the movement of at least first source 12 and the first detector 14, and may also include movement of the first support structure 90 and the rotatable extension 82. By way of further example, the first imager trajectory 130 may include information relating to the rotational directions represented by arrows 84 and 88 in FIG. 2. This first imager trajectory 130 may be referred to as an input trajectory, and may be updated by the system controller 48 based on other of the variables 122, 124. The first imager trajectory 130 may also be represented as a set of coordinates in a space corresponding to the first source 12 as a function of time, where the first source 12 traces a path defined by a line connecting the first X-ray source 12 with an iso-center of the imaged volume as the first X-ray source 12 moves about the imaged volume from a first time point of the first acquisition to a second time point of the first acquisition.

The second imager trajectory 132 may also be similarly represented by its respective X-ray source and time period of its respective acquisition. Thus, the second imagery trajectory 132 may also include, but is not limited to, the various rotational directions of the second imager 32. For example, the second imager trajectory 132 may include information relating to the path traversed by the second source and detector 22, 24 during a particular sequence. Like the first imager trajectory 130, the second imager trajectory 132 may be an input trajectory that is updated by the system controller 48 based on the other variables 122, 124, or may be a calculated trajectory after all other variables have been accounted for.

The first and second sets of variables 122, 124 are also illustrated as including a first imager sample rate 134 and a second imager sample rate 136. The first imager sample rate 134 and the second imager rate 136 may represent speed of movement of the first imager 30 and the second imager 32 respectively, or, additionally or alternatively, may represent the rate at which data is acquired by the imagers. In this respect, the first and second sets of variables 122, 124 may also include a number of acquisitions for the first imager 138 and a number of acquisitions for the second imager 140 based on the trajectory, speed, and sample rate of the imagers.

A first imager imaging mode 142 and a second imager imaging mode 144 may also be inputs to the system controller 48 for ultimately determining the manner in which the first imager 30 and the second imager 32 are controlled. For example, the first imager imaging mode 142 and second imager imaging mode 144 may be tomographic, projection, fluoroscopic, or the like. Various other parameters relating to the imaging mode may also be provided, such as X-ray technique parameters (kV, mAs, pulse width, dual energy mode, etc.), whether the imaging is being performed pre-interventionally, during a dynamic process (e.g., a process involving the use of a contrast agent, the introduction of a device such as a surgical instrument), or the like.

As noted above with respect to FIG. 2, a space-time occupancy model for both the first and second imagers 146, 148 may be generated or may be utilized by the system controller 148 to determine the particular manner in which the first imager 30 and the second imager 32 are controlled. For example, the system controller 48, in one embodiment, may generate the first imager space-time model 146 using the first imager configuration 126, the first imager trajectory 130, and the speed at which the imager 30 may move based on a desired sample rate for the first imager (represented as 134 above). The system controller 48 may generate the second imager space-time model 148 using similar respective factors. Thus, the system controller 48 may utilize the second imager configuration 128, the second imager trajectory 132, the second imager sample rate 136, and other variables, in order to generate the space-time model for the second imager 32. As discussed herein, the space-time models for the first imager 30 and the second imager 32 are models that may be generated using any suitable algorithms performed by the system controller 48 that represent the occupancy of space based on a particular point in time during the performance of the particular type of acquisition by the imagers. The space-time models may include a look up table, or similar feature, that includes a set of coordinates with one or more established coordinate frames occupied by the first imager 30 and the second imager 32, as a function of a point in time during a particular imaging sequence.

Furthermore, in one embodiment, the system controller 48 may generate these space-time models before the performance of particular acquisition sequences by the first and second imagers 30, 32 in order to determine whether the two imagers might collide or might obtain data in a way that interferes with one another. In such an embodiment, the system controller 48 may modify the space-time models in order to solve for trajectories for the first and second imagers 30, 32 that obtain a desired result (e.g., collision avoidance, signal contamination avoidance, desired acquisition time, or any combination of these or other effects).

As illustrated in FIG. 3, using the first set of variables 122, and in some embodiments, based on a relationship 150 with the second set of variables 124, the system controller 148 may generate a first imager sequence 152. Likewise, the system controller 48 may utilize the second set of variables 124, and in some embodiments, based on the relationship 150 with the first set of variables 122, may generate a second imager sequence 154. Based on the first and second imager sequences 152, 154, the system controller 148 may perform a synchronization 156 between the first and second imagers 30, 32. For example, the system controller 48 may control the activation of the first source 12 and the second source 22 as well as data acquisition by the first detector 14 and the second detector 24 in order to obtain two separate and desired sets of data. As noted above, the system controller 48 may utilize these two sets of data in order to generate a single three-dimensional image, or may use the separate sets of data in order to construct entirely separate sets of images.

In certain embodiments, the system controller 48 may utilize, in addition to the first and second sets of variables 122, 124, encoder feedback 98, 108 generated by the positional encoders 96, 106, respectively. In this way, the system controller 48 not only performs a predetermined analysis of the trajectory and space-time occupancy of the first and second imagers 30, 32, but also obtains real-time feedback in order to determine whether the modeled trajectories and the modeled acquisitions are being acquired in the manner for which the imaging sequences 152, 154 are designed.

Figure 4:
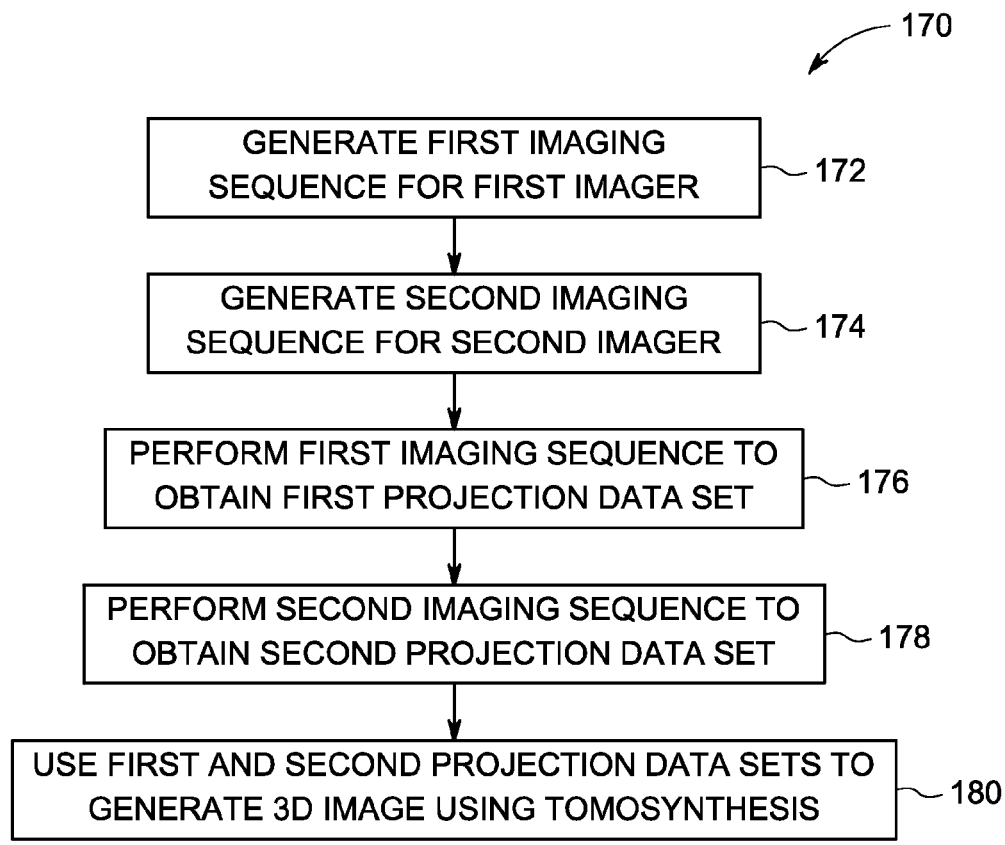
FIG. 4 is a process flow diagram depicting an embodiment of method of performing bi-plane tomographic imaging using the system of FIGS. 1 and 2, in accordance with aspects of the present disclosure.

With foregoing in mind, FIG. 4 depicts an example workflow performed by the system controller 48 before, during, and/or after a sequence in which data sets are obtained using the first and second imagers 30, 32. In particular, FIG. 4 depicts a method 170 of obtaining a volumetric (three-dimensional) image using the first and second imagers 30, 32 in accordance with the present techniques. The method 170 includes generating (block 172) the first imaging sequence for the first imager. The acts represented by block 172 may include utilizing any one or a combination of the variables described above with respect to FIG. 3, in any sequence, to generate the first imager sequence 152.

The method 170 may also include, before, during, or after the acts represented by block 172, generating (block 174) the second imaging sequence for the second imager 32. The acts represented by block 174 may include utilizing any one or a combination of variables described above with respect to FIG. 3, in any sequence, in order to generate the second imaging sequence 154.

The method 170 may also include performing (block 176) the first imaging sequence to obtain a first projection data set. As an example of the manner in which the system controller 48 may utilize the first imager 30 to perform the acts represented by block 176, the system controller 48 may displace the first source 12 and the first detector 14 along various trajectories in order to obtain data from a variety of projection directions. For example, with reference to FIG. 2, the system controller 48 may cause the rotatable extension 82 to rotate the first source 12 and the first detector 14 about the second axis of rotation 42 and, at substantially the same time, may also cause the first moving structure 86 to rotate the first source 12 and the first detector 14 about the third axis of rotation 44. In doing so, the system controller 48 causes the first source 12 and the first detector 14 to be rotated about 2 axes of rotation in order to obtain projection data from positions disposed along the frontal plane of the patient in a manner that is amenable to reconstruction using tomosynthesis algorithms. In other words, the system controller 48 may displace the first source 12 and the first detector 14 along a trajectory that is amenable to tomosynthesis (generated by a trajectory moving along the sphere having the iso-center).

The method 170 may also include performing (block 178) the second imaging sequence to obtain a second projection data set. The acts represented by block 178 may include performing an acquisition using the second imager 32 to obtain the second projection data set. For example, in one embodiment, the system controller 48 may coordinate the first imaging sequence and the second imaging sequence in obtaining the first and second projection data sets. Accordingly, in such an embodiment, the acts represented by block 178 may be performed before, during, or after performing the acts represented by block 176, for example by completing the first imaging sequence first, completing the second imaging sequence first, or interleaving the acquisitions of the first and second imaging sequences.

The second imaging sequence according to block 178 may be any imaging sequence suitable for performance by the second source 22 and the second detector 24. For example, the second imaging sequence may include a linear trajectory along which the second source 22 and the second detector 24 obtain projection images (e.g., along the rotational direction 104 (FIG. 2), or a line along the sphere having the iso-center). In other embodiments, the second imaging sequence may include moving the second source 22 and the second detector 24 about the rotational directional 104 and, alternatively, may include moving the second source 22 and the second detector 24 along one or more different rotational directions, translational directions, or the like. In still further embodiments, the second imager 32 may not be moved/may remain stationary. For instance, the second imager 32 may acquire data at a single projection position for each time the first X-ray source and the first X-ray detector completes all or less than all (e.g., a portion) of its trajectory, where a portion of the trajectory may include a section of the trajectory (e.g., a particular section of a path traced by the first X-ray source 12, or the path of the X-ray source 12 over a first period of time of the trajectory, or both).

It should be noted that the acts represented by the method 170 may be performed once—for example to obtain a single volumetric representation of the patient 18, or maybe performed multiple times, for example, to obtain multiple images of the patient. Further still, in certain embodiments, the method 170 may be performed on a substantially continuous basis, such as during an interventional procedure. For example, the first projection data set may be obtained on a substantially continuous basis and the second projection dataset may be obtained either on a substantially continuous basis as well, or on a more periodic basis. In such situations, the first projection data set may be supplemented with the second projection data set, for example such that the data is combined, or such that the second projection data set is used to update previously-generated images.

Figure 5:
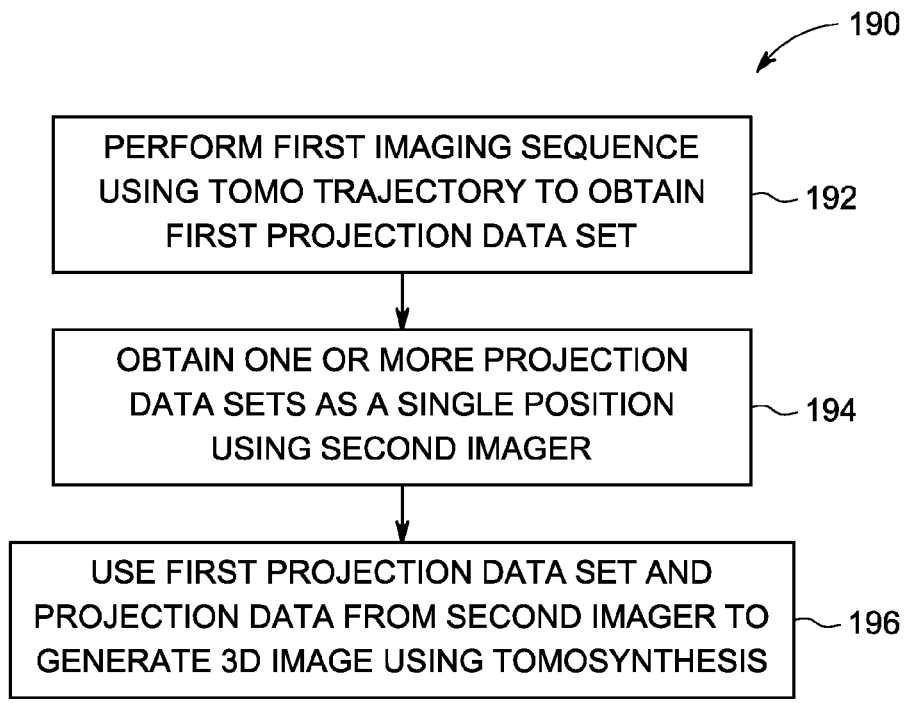
FIG. 5 is a process flow diagram depicting an embodiment of a method of performing bi-plane tomographic imaging in which the first imager of FIGS. 1 and 2 is used to perform a first trajectory and the second imager of FIGS. 1 and 2 is used to obtain single projection images from a single position, in accordance with aspects of the present disclosure.

FIG. 5 illustrates an embodiment of a method 190 for performing an imaging sequence in which the first imager 30 and the second imager 32 are used to generate a volumetric image. The method 190 includes performing (block 192) a first imaging sequence using the first imager 30. The acts represented by block 192 may include traversing a tomographic trajectory using the first imager 32. Traversing the tomographic trajectory according to block 192 may include obtaining a first data set representing X-ray attenuation data obtained from projection directions (represented by trajectory traced by the first X-ray source 12) that trace a line or another, more complex geometry along the sphere having the iso-center of the imaged volume. The tomographic trajectory may include a configuration in which the first source 12 remains below the patient table 92 and the first detector 14 remains above the patient table 92. In this configuration, there may be a substantially continuous orbit for dynamic volumetric (three-dimensional) imaging. In other words, the first source 12 and the first detector 14 may continuously move through the tomographic trajectory, movement e.g., as multiple consecutive "orbits" through a circular trajectory.

In certain embodiments, the tomographic trajectory traced by the first imager 30 may not necessarily cover the full range of acquisition positions that may be desirable in order to obtain the best image quality. Therefore, in certain embodiments, it may be desirable to supplement the first projection data set with additional data in order to provide a more complete set of information for tomosynthesis.

The method 190 may, therefore, also include obtaining (block 194) one or more projection images (e.g., 2-D fluoroscopic images) or projection data (e.g., raw or processed data) using the second imager. The acts represented by block 194 may include obtaining the one or more projection images using the second imager 32 at a single position. In other words, the second imager 32 may remain stationary. In other embodiments, the second imager 32 may move along the rotational direction 104, but may obtain only a single projection for every set of projection data that the first imager 30 acquires in traversing the tomographic trajectory a single time.

Once a desired or a suitable amount of projection data is obtained, the method 190 may include using the data obtained by the first imager 30 and the second imager 32 to generate (block 196) one or more volumetric images using tomosynthesis. For example, the first image set obtained by the first imager 30 may be supplemented by one or more projection images or sets of projection data obtained at a single position by the second imager 32. By way of non-limiting example, the tomosynthesis may be performed by iterative or analytical methods, which will be apparent to those of skill in the art.

Figure 6:
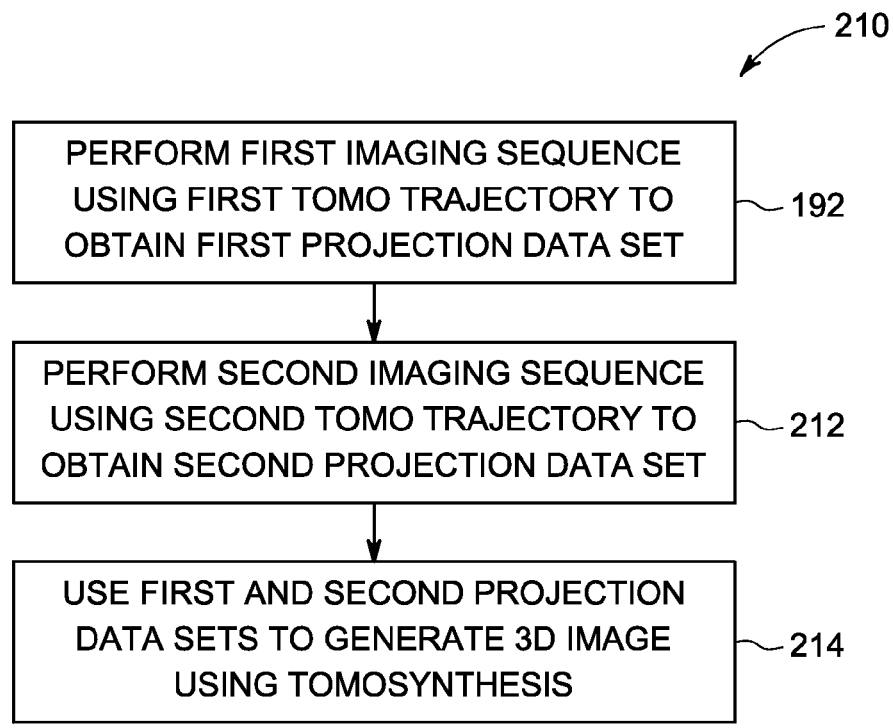
FIG. 6 is a process flow diagram depicting an embodiment of a method of performing bi-plane tomographic imaging in which the first imager of FIGS. 1 and 2 is used to perform a first trajectory to obtain data and the second imager of FIGS. 1 and 2 is used to perform a second trajectory to obtain data, in accordance with aspects of the present disclosure.

It should be noted that either or both of the first and second imagers 30, 32 may use a tomographic trajectory to obtain data. FIG. 6 depicts an embodiment of a method 210 in which both imagers use a tomographic trajectory in order to obtain projection data. The method 210 includes performing (block 192) the first imaging sequence using a first tomo trajectory to obtain a first data set. The acts represented by block 192 may be substantially the same as those described above with respect to FIG. 5 in block 192. However, in certain embodiments, the first tomo trajectory may be an incomplete trajectory (for example, half a trajectory, a quarter of a trajectory, or the like).

The method 210 also includes performing (block 212) a second imaging sequence using a second tomographic trajectory to obtain a second projection data set. The acts represented by block 212 may be performed by the second imager 32, for example by following an entirely different trajectory, or by following another portion of the trajectory if the first tomographic trajectory is incomplete. In other words, the trajectory traced by the first imager 30 and the trajectory traced by the second imager 30 may, when combined, produce a complete (e.g., continuous) trajectory. For example, the first trajectory may cover an angular displacement about the second axis of rotation 52 ranging from rest (denoted as 0 degrees, and is shown in FIG. 2) to a maximum angular displacement of approximately 70 degrees (e.g., clockwise), and the second trajectory may cover an angular displacement about the second axis of rotation 42 ranging from approximately 70 degrees to 120 degrees (e.g., clockwise) at maximum angular displacement, thereby covering an additional 50 degrees. When combined, the two trajectories may cover from 0 to 120 degrees. In certain embodiments, the two trajectories may overlap to a certain extent to allow for a handoff between the imaging chains.

The second tomographic trajectory may be symmetrical or asymmetrical, and may involve a rotation about a single axis or a rotation about one or more axes (ex. 2, 3, or more). For example, the second tomographic trajectory may include an arcuate path (i.e., the beam line of the second X-ray source 22 traces a line along the sphere having the iso-center), a circular or semi-circular path, an ellipsoidal or semi-ellipsoidal path (i.e., the beam line of the second X-ray source 22 traces a circle, semi-circle, ellipse, or semi-ellipse along the sphere having the iso-center of the imaged volume), or the like.

Thus, in a general sense, in performing the acts represented by blocks 192 and 212, the system controller 48 may cause either or both imagers to perform symmetrical tomographic trajectories. However, in other embodiments, the system controller 48 may cause the first and second imagers 30, 32 to perform a symmetric tomographic trajectory, using more acquisition points for one imager as opposed to the other, or using the same number of acquisition points for both imagers. In further embodiments, the trajectories may be the same or different, and the spacing between the acquisition points for both imagers may be the same or different. By way of non-limiting example, the first tomographic trajectory may represent a circular path, while the second tomographic trajectory may represent an ellipsoidal path or an arced path.

Once an appropriate amount of data is obtained using the first and second imagers 30, 32, the method 210 may include using (block 214) the first projection data set obtained by the first imager 30 and the second projection data set obtained by the second imager 32 to generate one or more volumetric images using tomosynthesis. The acts represented by block 214 may be substantially the same as those described above with respect to block 196 in FIG. 5, and may involve adding or otherwise combining the data acquired using the first imager 30 with the data acquired using the second imager 32, either pre- or post-tomosynthesis.

Figure 7:
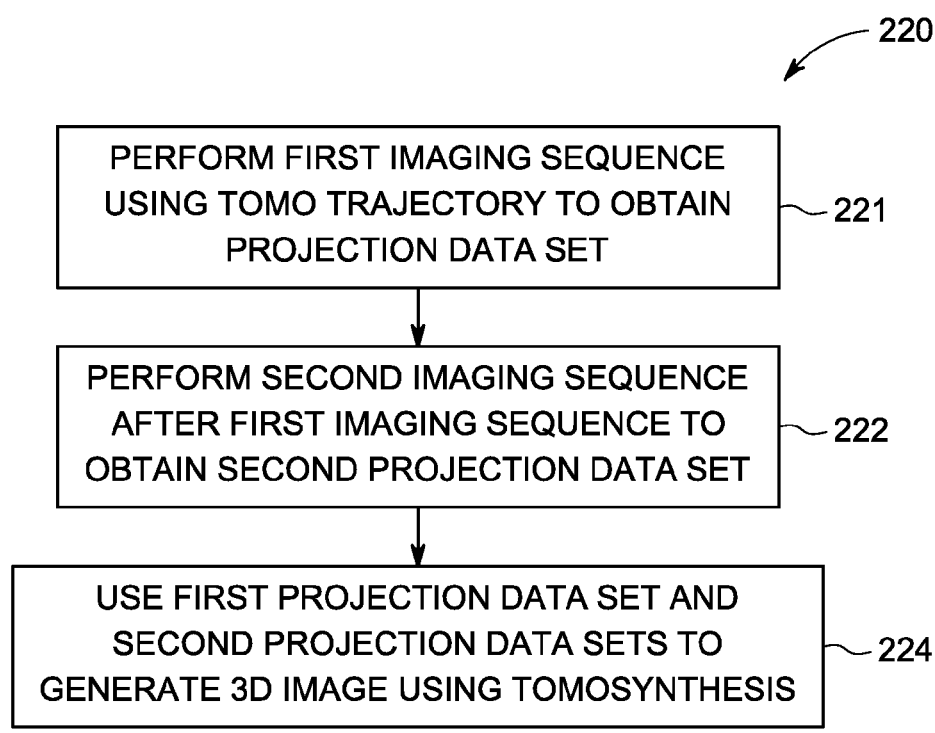
FIG. 7 is a process flow diagram depicting an embodiment of a method of performing bi-plane tomographic imaging in which the first imager of FIGS. 1 and 2 is used to perform a first trajectory to obtain data before a sequence performed by the second imager, in accordance with aspects of the present disclosure.

In accordance with certain embodiments of the present disclosure, the system controller 48 may use different temporal sequences for the acquisitions performed by the first imager 30 and the second imager 32. In other words, projections can be acquired in an alternating fashion using the imagers, or a full acquisition may be performed using the first imager 30, followed by a full acquisition using the second imager 32. Further, a variable number of projections can be acquired using the first imager 30, followed by a different number of acquisition points on using the second imager 32. FIG. 7 depicts an embodiment of a method 220 where the system controller 48 uses a temporal sequence in which first data is acquired before second data.

In the depicted embodiment, the method 220 includes performing (block 221) a first imaging sequence using a tomographic trajectory to obtain a first projection data set. The acts represented by block 221 may be substantially the same as those described above with respect to block 192 in FIG. 5, or may involve obtaining a certain number of projections from different positions using the first imager 30 interleaved with obtaining a certain number of projections using the second imager 32.

Accordingly, the method 220 may also include performing (block 222) a second imaging sequence after performing the first imaging sequence in accordance with block 221 to obtain a second projection data set. The acts represented by block 222 may include the acquisition of a single projection using the second imager 32 after acquiring a single projection using the first imager 30. Additionally or alternatively, the acts represented by block 222 may include obtaining one or more projection data sets using the second imager 32 after obtaining all desired projection data using the first imager 30.

It should be noted that the system controller 48 may control the acquisitions performed by the first and second imagers 30, 32 in a variable manner. For example, the number of projection acquisitions can be changed each time one of the imagers completes its respective trajectory. By way of example, this may include performing a first number of acquisitions using the first imager 30 and a first tomographic trajectory, and then obtaining a second number of projection images (or sets of projection data) using the second imager 32 and a second trajectory. This may be followed by obtaining a different number of projections using the first imager 30, for example, using the same or different trajectories compared to the first trajectory performed by the first imager 30. In such embodiments, this particular type of sequence may be performed a number of different times to obtain appropriate amounts of data, and may enable the acquisition of real-time patient information, for example, during an interventional procedure, or may enable the real-time manipulation of acquisition parameters (e.g., by an operator) in order to vary the portion of the patient 18 being imaged, or in order to obtain a visualization of a dynamic process within the patient 18 (e.g., a process to monitor the perfusion of a contrast agent through the patient 18).

The method 220 may also include using (block 224) the first projection data set and the second projection data set acquired according to blocks 221 and 222 to generate one or more volumetric images using tomosynthesis. The acts represented by block 224 may be substantially the same as those described above with respect to block 196 in FIG. 5. However, it should be noted that the manner in which the system controller 48 (or another computing device used for tomosynthesis) performs reconstruction or synthesis may depend on the manner in which data is acquired using the first and second imagers 30, 32. For instance, the system controller 48 or other computing device may perform tomosynthesis in a real time manner during an interventional procedure after receiving appropriate amounts of data, and/or may perform substantially real time updates on a synthesized volumetric image as new data is acquired.

Figure 8:
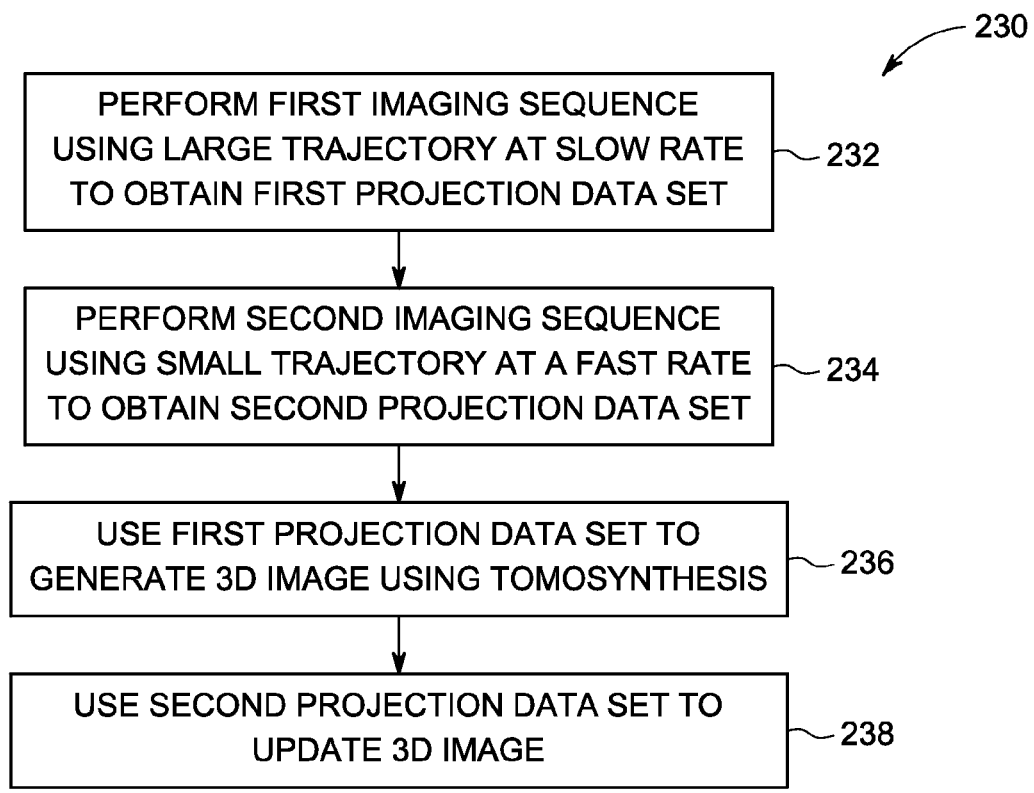
FIG. 8 is a process flow diagram depicting an embodiment of a method of performing bi-plane tomographic imaging in which the first imager of FIGS. 1 and 2 is used to perform a first, relatively large trajectory at a relatively slow rate to obtain data and the second imager of FIGS. 1 and 2 is used to perform a second, relatively small trajectory at a relatively slow rate to obtain data used as updates for images produced using the data collected by the first imager, in accordance with aspects of the present disclosure.

Indeed, the present disclosure also includes embodiments where the system controller 48 uses different tomographic trajectories and different rates of acquisition to provide high-resolution and rapid images of a patient (e.g., during a procedure). FIG. 8 depicts an embodiment of a method 230 for performing such an imaging procedure. In particular, the method 230 includes performing (block 232) a first imaging sequence in which the first imager 30 follows a first trajectory. In certain embodiments, the first trajectory may be a large trajectory, and the speed of the first imager 30 along the trajectory may be relatively slow, and/or the orbit time (i.e., the time to complete one cycle through the trajectory) may be relatively long. The first trajectory may be any suitable trajectory for obtaining X-ray attenuation data amenable to tomosynthesis, such as a circular trajectory, an ellipsoidal trajectory, or any combination of paths that are enabled by the first imager 30 (e.g., any combination and extent of the rotational directions 84, 88 (FIG. 2)). The movement of the first imager 30 along the first trajectory may be at a first rate, which may be determined by the rate at which the projection data is obtained and the size of the trajectory, as well as the trajectory and rate of the second imager 32, as discussed below.

The method 230 may also include performing (block 234) a second imaging sequence using the second imager 32. In the second imaging sequence represented by block 234, the second imager 32 may use a second trajectory, which may be larger, substantially the same size, or smaller than the trajectory of the first imager 30 (e.g., a smaller circle, ellipse, or the like). Further, the second imager 32 may move along the second trajectory at a second rate, which may be faster than the first rate at which the first imager 30 moves along its trajectory.

The method 230 may include performing the acts represented by blocks 232 and 234 at substantially the same time. For example, the first imager 30 may move along the first trajectory while obtaining projection data at a first data acquisition rate. Substantially simultaneously, the second imager 32 may move along a smaller, second trajectory while obtaining projection data at the second acquisition rate (which may be faster than the first acquisition rate). In one embodiment, the first acquisition rate may be slower for the larger, first trajectory, while the second acquisition rate may be faster for the smaller, second trajectory.

In certain embodiments, the method 230 may include using the first projection data set acquired by the first imager 30 to generate (block 236) a 3-D image using tomosynthesis. For example, data acquired using the first imager may be used to generate a high resolution image, although the data acquisition may be relatively slow compared to the acquisition performed by the second imager 30.

Indeed, in certain embodiments, the data acquired using the second imager 32 may be used to update (block 238) the high-resolution image. Therefore, in such embodiments, the first imager 30 may be used to produce a high resolution image, and the second imager 32 may be used to provide rapid updates to the high resolution image, for example to account for patient movement or contrast agent perfusion within the tissue.

As an example workflow, the first imager 30 may trace a large circle at a relatively slow rate, which may provide greater angular coverage, and the second imager 32 may trace a small circle at a relatively faster rate to obtain rapid updates. As one non-limiting example, the first imager 30 may perform its acquisition at 30 frames per second (e.g., the first acquisition rate), while the second imager 32 performs its acquisition at 60 frames per second (e.g., the second acquisition rate, which is faster than the first acquisition rate). In this example, the acquisitions may also be interleaved. For instance, if b1 represents an acquisition using a first beam line produced by the first imager 30 and b2 represents an acquisition using a second beam line produced by the second imager 32, an example sequence may involve b1, b2, b2, b2, b1, b2, b2, b2, and so on, until the particular imaging procedure is completed.

In accordance with the present disclosure, each of the first and second imagers 30, 32 may perform more than one type of acquisition, depending on the particular situation. For example, in some embodiments, a first configuration may be utilized before an interventional procedure or before a contrast agent injection, a second configuration may be utilized during the interventional procedure or while the contrast agent is perfusing in the patient 18, and a third configuration may be utilized after the interventional procedure or after the agent has been expelled or is no longer viable. Other combinations are also possible. For example, only pre- and intra-interventional acquisitions may be performed, or only intra- and post-interventional procedures may be performed using different acquisition parameters (e.g., different scan configurations).

Figure 9:
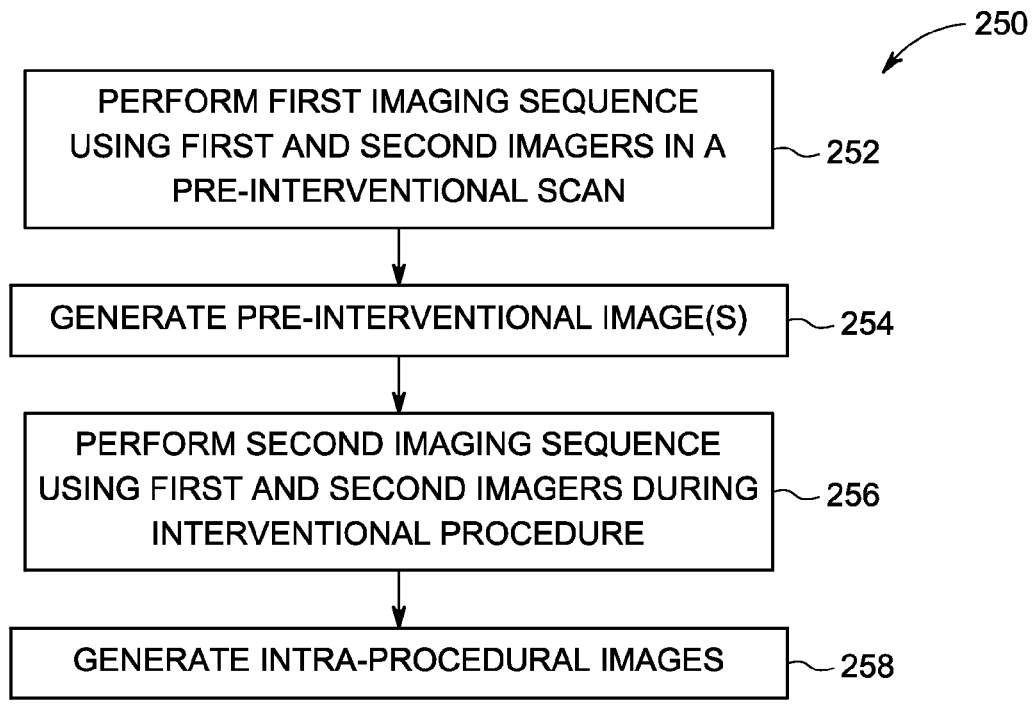
FIG. 9 is a process flow diagram depicting an embodiment of a method of performing bi-plane tomographic imaging both pre- and intra-interventionally, in which the first and imagers of FIGS. 1 and 2 are used to perform a first bi-plane tomographic sequence before an interventional procedure to obtain a pre-interventional volumetric image, and the first and second imagers are used to obtain data to update the pre-interventional image during the interventional procedure, in accordance with aspects of the present disclosure.

An embodiment of a method 250 for performing different scan configurations at different interventional stages is depicted in FIG. 9. Specifically, the method 250 includes performing (block 252) a first imaging sequence (or a first imaging configuration) using the first and second imagers 30, 32 in a pre-interventional scan (or before contrast agent is injected), a so-called baseline scan. The acts represented by block 252 may include a first trajectory and a first acquisition rate for the first imager 30 and a second trajectory and a second acquisition rate for the second imager 32.

The data acquired during the first imaging sequence may be used to generate (block 254) one or more pre-interventional images. For example, the data acquired using the first imager 30 may be used to generate one or more first images, and the data acquired using the second imager 32 may be used to generate one or more second images. Alternatively or additionally, the data acquired using the first and second imagers 30, 32 may be used to generate one or more first images (e.g., where data acquired on one of the imagers is used to supplement the other).

The method 250 may then include performing (block 256) a second imaging sequence, which may include a second imaging configuration. The second imaging configuration may include a third trajectory and a third acquisition rate for the first imager 30, and a fourth trajectory and a fourth acquisition rate for the second imager 32. The third trajectory and the third acquisition rate may, individually, be the same or different when compared to the first trajectory and the first acquisition rate, respectively, performed in accordance with block 252 by the first imager 30. Likewise, the fourth trajectory and the fourth acquisition rate may, individually, be the same or different when compared to the second trajectory and the second acquisition rate, respectively, performed in accordance with block 252 by the second imager 32.

The data acquired during the second imaging sequence may be used to generate (block 258) one or more intra-interventional images (or images that enable the monitoring of contrast agent perfusion). For example, the data acquired using the first imager 30 may be used to generate one or more third images, and the data acquired using the second imager 32 may be used to generate one or more fourth images. Alternatively or additionally, the data acquired using the first and second imagers 30, 32 may be used to generate one or more second images (e.g., where data acquired on one of the imagers is used to supplement the other). Further still, the data acquired in the second imaging sequence may, in certain embodiments, be used to update the one or more first images obtained pre-interventionally. In another embodiment, at least one trajectory is acquired with one or both imagers before the injection of contrast, and after the contrast injection one or more trajectories are acquired, where the pre-injection and post-injection trajectories have at least a subset of projection angles in common. This way, one can generate datasets including subtracted projection images (where the overlying anatomy has been removed through the subtraction process) and one or more 3D volume images may be generated based on the subtracted dataset(s).

Figure 10:
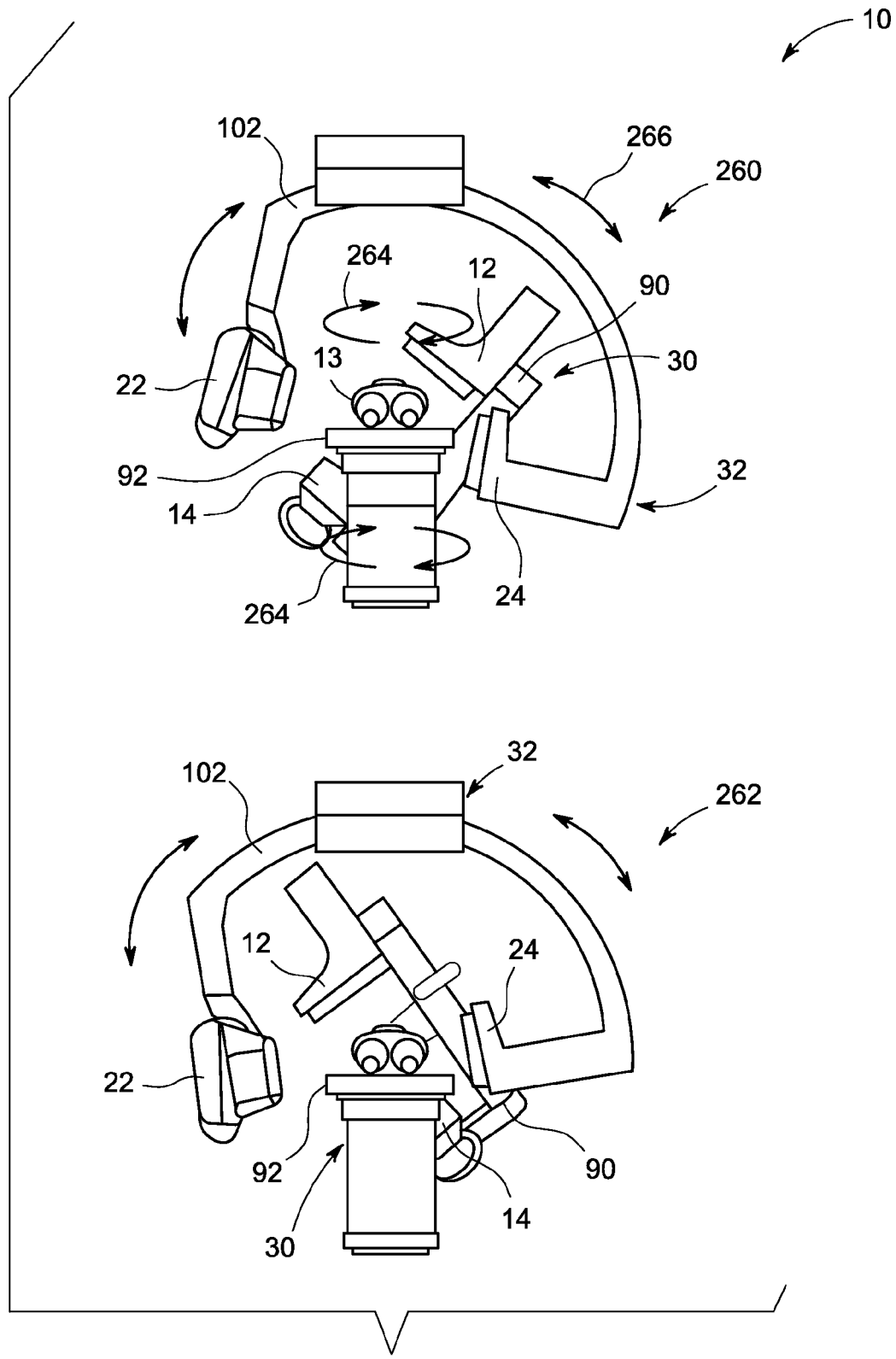
FIG. 10 is an end view of an example configuration of the system of FIGS. 1 and 2 at different points in time, the configurations depicting the relative movement of the first and second imagers during a bi-plane tomographic imaging sequence, in accordance with aspects of the present disclosure.

In any one or a combination of the methods described above with respect to FIGS. 4-9, the system controller 48 may control the movement of the first and second imagers 30, 32 to maintain a certain degree of separation between them (e.g., to avoid collision and/or signal contamination). An example configuration is depicted in FIG. 10 as an end view of the system 10, including the first and second imagers 30, 32 positioned at different points during a bi-plane acquisition—specifically a first time point configuration 260 and a second time point configuration 262, which represent first and second points in time, respectively, during an example bi-plane acquisition.

In embodiments where the first imager 30 is used in a frontal plane tomo mode, as shown in the first and second time point configurations 260, 262, the structures of the first imager 30 move in a synchronized fashion in order to achieve a circular or elliptical frontal plane tomo trajectory 264 of the first source and detector 12, 14 relative to the plane defined by the patient table 92 (i.e., such that the first X-ray source 12 generates a trajectory that traces a non-linear shape on the sphere having the iso-center of the imaged volume), as discussed above. In the presence of a laterally positioned imager (in this example, the second imager 30), the available travel space of the first source and detector 12, 14 may be limited by the potential collision of the first support structure 90 with the second detector 24. In certain embodiments, the system controller 48 may apply a swing motion trajectory 266 (where a trajectory generated by the second X-ray source 22 traces a line on the sphere) on the second imager 32 (e.g., to the second support structure 102 such as a gantry) synchronized with the frontal plane tomo trajectory 264 in order to clear the motion space of the first support structure 90. As a result, the system 10 can perform bi-plane tomo acquisitions with larger frontal plane tomo angles for the first imager 30. The collision avoidance strategy may be based on a space/time occupancy model of the first and second imagers 30, 32 and the position feedback 96, 106 from the encoders (e.g., gantry encoders). This may enable calculation of the optimal collision avoidance trajectory for the second imager 30 while increasing the tomo angle on the first imager 30 (e.g., enabling a maximum or unconstrained angular displacement). The trajectories may further be optimized such as to minimize the amount of missing data.

Figure 11:
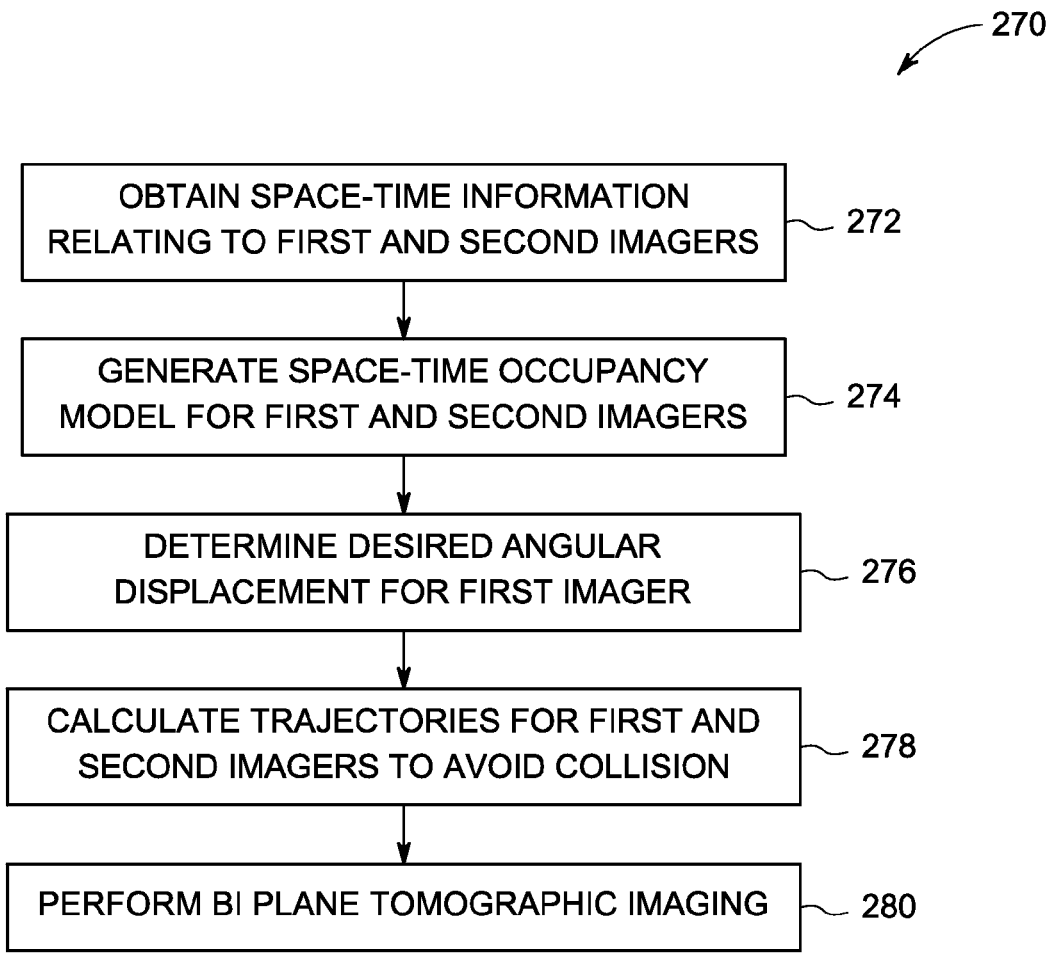
FIG. 11 is a process flow diagram depicting an embodiment of a method of performing bi-plane tomographic imaging in which one or more space-time occupancy models are generated for the first and imagers of FIGS. 1 and 2, and the one or more models are used to perform a bi-plane tomographic sequence, in accordance with aspects of the present disclosure.

FIG. 11 is a process flow diagram depicting an embodiment of a method 270 that the system controller 48 may perform during any one or a combination of the acquisition methods above in order to enable the collision avoidance strategy noted above. The method 270 includes obtaining (block 272) space-time information relating to the first and second imagers 30, 32. The acts represented by block 272 may include an input (e.g., user-provided input or input from the encoders 96, 106), such as any one or a combination of the variables 122, 124 discussed above with respect to FIG. 3, relating to the size of the first and second imagers 30, 32, the respective trajectories of the first and second imagers 30, 32 for a particular type of acquisition, the rate of movement of the imagers 30, 32 along their respective trajectories during a particular type of acquisition, and so on.

In certain embodiments, as discussed above with respect to FIG. 3, the system controller 48 (or other processing device) may generate (block 274) a space-time occupancy model for the first and second imagers 30, 32. This may include the generation of positional information relating to the first imager 30 and the second imager 32 (e.g., coordinates within a coordinate frame corresponding to physical features of the first imager 30 and/or the second imager 32) as a function of time during an imaging sequence performed by the first imager 30 and the second imager 32. For example, the model may include a look up table or similar information that is generated by, in one embodiment, denoting the coordinates within the coordinate frame occupied by the physical features of the first imager 30, the occupancy being constrained by the trajectory of the first imager 30 over the time of a particular type of acquisition. In this example, the model may also include an additional look up table or similar information that is generated by, in one embodiment, denoting the coordinates within the coordinate frame occupied by the physical features of the second imager 32, the occupancy being constrained by the trajectory of the second imager 32 over the time of the particular type of acquisition.

As an example, the space-time occupancy information relating to the first imager 30 may include a set of coordinates representing the space occupied by the first imager 30 (e.g., the first source 12, the first detector 14, and/or the first support structure 90 of the first imager 30) at various time points during an acquisition sequence. In this way, the model enables the system controller 48 to anticipate the position of the first imager 30 during a given imaging sequence.

Similarly, the space-time occupancy information relating to the second imager 32 may include a set of coordinates representing the space occupied by the second imager 32 (e.g., the second source 22, the second detector 24, and/or the second support structure 102 of the second imager 32) at various time points during an acquisition sequence. In this way, the model enables the system controller 48 to anticipate the position of the second imager 32 during a given imaging sequence.

The system controller 48 may modify aspects of the model in order to obtain a particular result. For example, the system controller 48 may modify the trajectory of the first and/or second imager 30, 32, the speed of movement of the first and second imagers 30, 32, their respective acquisition rates, and the like. Indeed, in one embodiment of the method 270, the system controller 48 may use information relating to the first imager 30 (e.g., the size and/or freedom of movement of the first imager 30) to determine (block 276) a maximum angular displacement or other desired displacement for the first imager 30 during a given imaging sequence. In certain embodiments, it may be desirable to determine the maximum angular displacement of the first imager 30 because the first imager 30 may be used for higher resolution/higher quality images compared to the second imager 32. In such situations, it may be beneficial to obtain maximum angular coverage of the patient 18 using the first imager 30. The maximum angular displacement of the first imager 30, in some embodiments, may also be constrained by the space-time occupancy of the second imager 32, as provided/determined by the space-time occupancy model.

By way of non-limiting example, the maximum angular displacement for the first imager 30 may be a maximum angular displacement about the first rotational axis 40, the second rotational axis 42, or the third rotational axis 44, or respective angular displacements about any one or a combination of these axes of rotation. In accordance with certain embodiments, the first imager 30, for example with reference to FIG. 2, may have a maximum angular displacement (e.g., about the second rotational axis 42) from the x-y plane formed by the first and second rotational axes 40, 42 (e.g., such as represented by the sagittal/medial plane of the patient 18) of any angle, such as between approximately 20 and approximately 40 degrees, for example of approximately 35 degrees, in either or both directions represented by the double-headed arrow 84. Further, the displacement in either direction may be independent of the other direction (e.g., one direction of the arrow 84 versus the other direction of the arrow 84). For example, the first imager 30 may have a first angular displacement in a first direction of the arrow 84 (e.g., clockwise rotation) and a second angular displacement in a second direction of the arrow 84 (e.g., counterclockwise rotation), where the first and second angular displacements may be the same or different. As discussed above with respect to FIG. 2, the first imager 30 may, in certain embodiments, rotate about the second and third rotational axes 42, 44, and may have the same or different angular displacements about these axes, such as the angular displacements noted above.

The method 270 may also include updating or otherwise calculating (block 278) a trajectory (e.g., a new or updated trajectory) for either or both of the first and second imagers 30, 32. For example, in embodiments where the input obtained in block 272 includes a first trajectory for the first imager 30 and a second trajectory for the second imager 32, the first and/or the second trajectories may be updated using information provided by the space-time occupancy model (or models). For example, the trajectory adjustments may include constraints on angular displacements, variation in movement rate, and the like, in order to obtain a desired degree of angular separation between the imagers 30, 32 (e.g., in order to cover a large portion of the patient substantially simultaneously), to avoid both imagers 30, 32 from having projection directions that are close together at a certain point in time (e.g., to avoid signal contamination), and/or to maintain a desired degree of separation between the imagers 30, 32 to avoid collision.

In embodiments where the input obtained in accordance with block 272 does not include input trajectories, new trajectories may be calculated in accordance with block 278 in order to obtain X-ray projection data in a desired manner using both of the imagers 30, 32. It should be noted that either or both of the trajectories of the first and second imagers 30, 32 may be updated or newly generated, and in some embodiments may depend (at least partially) on the angular displacement determined in accordance with block 276. Once the new/updated trajectory or trajectories are generated, the method 270 may include performing (block 280) a bi-plane tomographic imaging process using the first and second imagers 30, 32.

Figure 12:
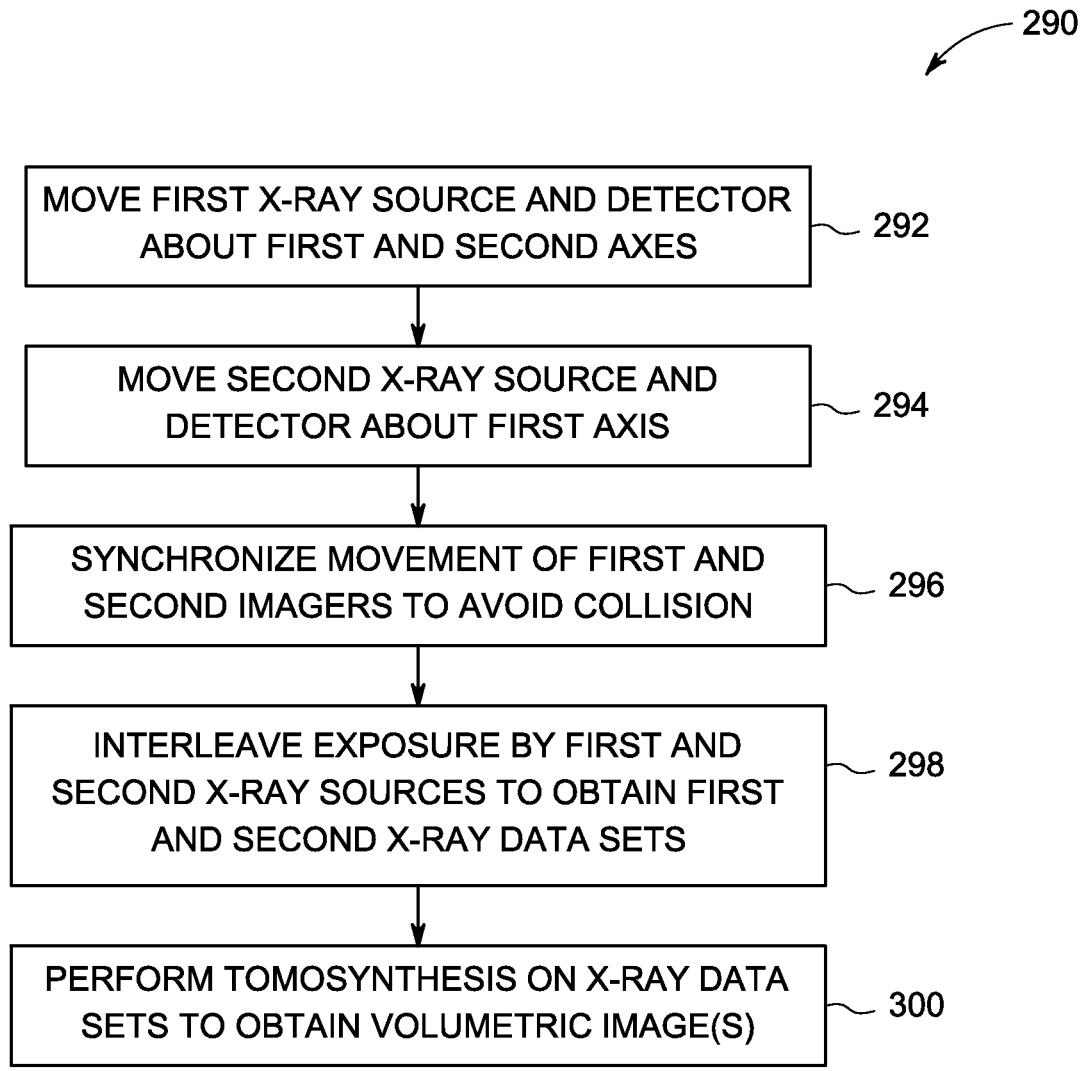
FIG. 12 is a process flow diagram depicting an embodiment of a method of performing bi-plane tomographic imaging in which the respective movements of the first and imagers of FIGS. 1 and 2 are coordinated to avoid collision, in accordance with aspects of the present disclosure.

An embodiment of a bi-plane tomographic method 290 is depicted as a block flow diagram in FIG. 12. The method 290 includes moving (block 292) the first source 12 and the first detector 14 (e.g., of the first imager 30) about first and second axes. With reference to FIG. 2, the first and second axes may be the second axis of rotation 24 and the third axis of rotation 44 (corresponding to rotation about the y- and z-axes), respectively.

In rotating about the second and third axes 42, 44, the trajectory followed by the first source 12 may be represented as a circle or an ellipse that remains below the patient 18, and the trajectory followed by the first detector 14 may also be represented as a circle or an ellipse that remains above the patient 18. In this way, the first imager 30 may obtain frontal plane images/attenuation data from a plurality of projection directions. However, because the angular displacement of the first imager 30 is not a full 180 degrees, frontal plane imaging performed by the first imager 30 may not necessarily generate certain angular data that would be beneficial for tomographic reconstruction. In accordance with present embodiments, imaging based on an additional plane using the second imager 32 may provide such data.

The method 290 also includes moving (block 294) the second source 22 and the second detector 24 about the first axis (e.g., the second axis of rotation 42). The acts represented by block 294 may include moving the second source and detector 22, 24 about the first axis and an additional axis (e.g., the second and third axes of rotation 42, 44), or may include moving the second source and detector 22, 24 only about the first axis (e.g., the second axis of rotation 42).

In rotating about the second axis of rotation 42, the trajectory followed by the second source 22 may be represented as an arc or semi-circle that remains on one side of the median (lateral) plane of the patient 18, and the trajectory followed by the second detector 24 may also be represented as an arc or semi-circle that remains on the opposite side of the median (lateral) plane of the patient 18. In this way, the second imager 30 may obtain lateral plane images/attenuation data from a plurality of projection directions.

The system controller 48, in performing the method 290, may also synchronize (block 296) the movement of the first and second sources 12, 22 and first and second detectors 14, 24 so as to avoid collision between the imagers. The acts represented by block 296 may include controlling the rate of movement of the imagers 30, 32, constraining angular displacement, or the like, based on, for example, one or more inputs from one or more space-time occupancy models for the first and second imagers 30, 32. The system controller 48 may perform the acts represented by block 296 by maintaining a certain degree of separation between the imagers 30, 32. The movement may additionally be synchronized to avoid obtaining projections from substantially the same perspectives at substantially the same time.

In this regard, the method 290 may also include interleaving (block 298) the exposure performed by the first and second sources 12, 22, for example in order to prevent signal contamination resulting from acquiring data with a detector that is not on the same imaging apparatus as the source that has generated the radiation. In other words, interleaving the exposure by the first and second imagers 30, 32 may avoid signal contamination resulting from the first detector 14 detecting radiation generated by the second source 22, and from the second detector 24 detecting radiation generated by the first source 12.

Once an appropriate amount of data is obtained (e.g., either during the procedure or after the procedure), tomosynthesis may be performed (block 300) on some or all of the acquired data. For example, the data acquired by the first imager 30 may include data generated from a plurality of frontal plane perspectives, and may be used as a main source of data for tomographic reconstruction (e.g., iterative or analytical reconstruction).

The acts represented by block 300 may also include utilizing the data generated by the second imager 32 for additional angular information (e.g., data obtained from projection directions representing a greater angular displacement than the first imager 30 performs). Indeed, the use of the second imager 32 to provide such supplemental data may reduce the need to scan the first imager 30 through additional angles, which can reduce scan time and X-ray dosage to the patient. Further, because the first and second imagers 30, 32 are independently controlled, the time to produce useful images (e.g., as in interventional procedures) may be reduced, since projection data can be obtained from different projection directions at substantially the same time.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical imaging system, comprising:
   a first X-ray imager comprising:
      a first structure supporting a first X-ray source and a first X-ray detector, wherein the first structure is configured to move the first X-ray source and the first X-ray detector about an imaged volume;
   a second X-ray imager positioned crosswise relative to the first X-ray imager, comprising:
      a second structure supporting a second X-ray source and a second X-ray detector; and
   an imaging control system comprising one or more tangible, non-transitory, machine-readable media collectively storing one or more sets of instructions executable by one or more processors to:
      move the first X-ray source along a first trajectory about the imaged volume while obtaining first X-ray attenuation data of the imaged volume via a first acquisition, wherein the first trajectory is non-linear and is represented by a first path traced by a line connecting the first X-ray source and an iso-center of the imaged volume as the first X-ray source moves about the imaged volume from a start of the first acquisition to an end of the first acquisition;
      obtain second X-ray attenuation data of the imaged volume via a second acquisition using the second X-ray source and the second X-ray detector; and
      synthesize a volumetric image from the first X-ray attenuation data using tomosynthesis and the second X-ray attenuation data.

2. The system of claim 1, wherein the first structure is configured to rotate the first X-ray source about at least first and second axes in order to move the first X-ray source along the first trajectory, and augment the first X-ray attenuation data from the first X-ray imager with the second X-ray attenuation data from the second X-ray imager to produce full data that creates the volumetric image.

3. The system of claim 1, wherein the one or more sets of instructions stored on the imaging control system, when executed by the one or more processors, are configured to control the second X-ray imager such that the second X-ray attenuation data is obtained from only one X-ray source position.

4. The system of claim 1, wherein the one or more sets of instructions stored on the imaging control system, when executed by the one or more processors, are configured to vary the first trajectory, or a second trajectory of the second imager, or a combination thereof, over time during the respective acquisition.

5. The system of claim 4, wherein the one or more sets of instructions stored on the imaging control system, when executed by the one or more processors, are configured to collect at least one of the first X-ray attenuation data, the second X-ray attenuation data, or a combination thereof, over less than the respective entire first trajectory and second trajectory.

6. The system of claim 4, wherein the one or more sets of instructions stored on the imaging control system, when executed by the one or more processors, are configured to rotate the first X-ray detector, the second X-ray detector, or a combination thereof, over at least a portion the first and second trajectories, respectively.

7. The system of claim 1, wherein the second structure is capable of moving the second X-ray source and the second X-ray detector together about a second trajectory about the imaged volume, wherein the second trajectory is represented by a second path traced by a line connecting the second X-ray source and the iso-center of the imaged volume as the second X-ray source moves about the imaged volume from a start of the second acquisition to the end of the second acquisition.

8. The system of claim 7, wherein the one or more sets of instructions stored on the imaging control system, when executed by the one or more processors, are configured to adapt the first trajectory of the first X-ray source to at least one input from an external source, wherein the at least one input comprises an input relating to the second X-ray imager, an input relating to a contrast agent perfusing through the imaged volume, an input relating to a physiological process occurring within the imaged volume, an input due to the presence or motion of a device within the imaged volume, an input due to patient motion or other physiological process, an operator input, or any combination thereof.

9. The system of claim 7, wherein the one or more sets of instructions stored on the imaging control system, when executed by the one or more processors, are configured to rotate the second X-ray source about at least a first axis in order to enable the first X-ray source to move along the first trajectory.

10. The system of claim 7, wherein the second path is linear.

11. The system of claim 7, wherein the one or more sets of instructions stored on the imaging control system, when executed by the one or more processors, are configured to coordinate movement of the first imager and the second imager such that the first and second imagers never occupy the same space.

12. The system of claim 7, wherein the one or more sets of instructions stored on the imaging control system, when executed by the one or more processors, are configured to coordinate movement of the first X-ray imager and the second X-ray imager so that they at least partially occupy the same space at different times over at least a portion of their respective trajectories.

13. The system of claim 12, wherein the one or more sets of instructions stored on the imaging control system, when executed by the one or more processors, are configured to coordinate movement of the first X-ray imager and the second X-ray imager by constraining movement of physical gantry motion axes of the first imager and the second imager, respectively.

14. The system of claim 12, wherein the one or more sets of instructions stored on the imaging control system, when executed by the one or more processors, are configured to coordinate movement of the first X-ray imager and the second X-ray imager so that their respective trajectories combine to produce a larger trajectory.

15. The system of claim 1, wherein the one or more sets of instructions stored on the imaging control system, when executed by the one or more processors, are configured to vary respective X-ray attenuation data acquisition parameters for at least one of the first and second X-ray imager such that their respective X-ray techniques, frame rates, movement rates through the respective first and second trajectories, or any combination thereof, are different.

16. The system of claim 1, wherein the one or more sets of instructions stored on the imaging control system, when executed by the one or more processors, are configured to vary respective X-ray attenuation data acquisition parameters of either or both of the first and second X-ray imagers over time.

17. The system of claim 16, wherein the respective X-ray attenuation data acquisition parameters comprise X-ray technique, frame rate, movement rate through the imager's respective trajectory, tomographic angle, or any combination thereof.

18. The system of claim 16, wherein the respective X-ray attenuation data acquisition parameters are adapted by the one or more sets of instructions as a function of one or more of physiologic events, a respective projection angle of the first or second X-ray source, feedback from one or more positional encoders of the first and/or second X-ray imagers, an operator input, or any combination thereof.

19. The system of claim 1, wherein the one or more sets of instructions stored on the imaging control system, when executed by the one or more processors, are configured to cause the first and/or second X-ray imagers to perform a dual energy acquisition.

20. The system of claim 1, wherein at least one of the first structure and the second structure comprises a C-arm or gantry supporting the respective X-ray source and X-ray detector.

21. A method, comprising:
in a bi-plane tomographic imaging system:
moving a first X-ray source and a first X-ray detector about first and second axes to generate a first trajectory while obtaining a plurality of first X-ray attenuation data sets from an imaged volume via a first acquisition, wherein first trajectory is represented by a non-linear path traced by a line connecting the first X-ray source with an iso-center of the imaged volume as the first X-ray source moves about the imaged volume from a first time point of the first acquisition to a second time point of the first acquisition;
obtaining a second X-ray attenuation data set from an imaged volume via a second acquisition using a second X-ray source and a second X-ray detector positioned crosswise with respect to the first X-ray source and the first X-ray detector; and
synthesizing a volumetric image using at least one of the plurality of first X-ray attenuation data sets using tomosythesis and the second X-ray attenuation data set as source data such that the first X-ray attenuation data from the first X-ray imager is augmented with the second X-ray attenuation data from the second X-ray imager to produce full data that creates the volumetric image.

22. The method of claim 21, wherein the second X-ray imager performs the second acquisition to obtain the second X-ray attenuation data set at a single projection position for each time the first X-ray source and the first X-ray detector complete a first portion of the first trajectory, wherein the first portion of the first trajectory comprises a first section of the non-linear path.

23. The method of claim 21, wherein the plurality of first X-ray attenuation data sets and the second X-ray attenuation data set are obtained using a first set of coordinated movements for the first and second X-ray imagers during a first imaging sequence, and additional X-ray attenuation data is obtained using a second set of coordinated movements for the first and second X-ray imagers in a second imaging sequence, wherein the first and second sets of coordinated movements are different, and the method is adapted to generate the second set of coordinated movements in response to an input relating to a contrast agent perfusing through the imaged volume, an input relating to a physiological process occurring within the imaged volume, feedback from one or more positional encoders of the first and/or second X-ray imagers, an operator input, or any combination thereof.

24. The method of claim 23, comprising:
moving the second X-ray source and the second X-ray detector together about at least the first axis and obtaining a plurality of second X ray attenuation data sets such that the second X-ray attenuation data set is one of the plurality of second X-ray attenuation data sets;
acquiring the plurality of first X-ray attenuation data sets at a first imager setting comprising at least a first acquisition rate and the first trajectory;
acquiring the plurality of second X-ray attenuation data sets at a second imager setting, wherein the second imager setting comprises at least one of an acquisition rate that is faster than the first acquisition rate and a second trajectory that is larger than the first acquisition trajectory; and
synthesizing volumetric images using at least some of the plurality of first X-ray attenuation data sets; and
continuously updating the synthesized volumetric images using at least one of the plurality of second X-ray attenuation data sets.

25. A medical imaging system, comprising:
a first X-ray imager comprising:
  a first structure supporting a first X-ray source and a first X-ray detector, wherein the first structure is configured to move the first X-ray source and the first X-ray detector about an imaged volume;
a second X-ray imager positioned crosswise relative to the first X-ray imager, comprising:
  a second structure supporting a second X-ray source and a second X-ray detector; and
an imaging control system comprising one or more tangible, non-transitory, machine-readable media collectively storing one or more sets of instructions executable by one or more processors to:
  move the first X-ray source along a first trajectory about the imaged volume while obtaining first X-ray attenuation data of the imaged volume, wherein the first trajectory is linear and is represented by a first path traced by a line connecting the first X-ray source and an iso-center of the imaged volume as the first X-ray source moves about the imaged volume;
  obtain second X-ray attenuation data of the imaged volume using the second X-ray source and the second X-ray detector while maintaining the second X-ray source and the second X-ray detector in a single position; and
  synthesize a volumetric image from the first X-ray attenuation data using tomosynthesis and the second X-ray attenuation data, such that the first X-ray attenuation data from the first X-ray imager is augmented with the second X-ray attenuation data from the second X-ray imager to produce full data that creates the volumetric image.

* * * * *

UNITED STATES PATENT AND TRADEMARK OFFICE
CERTIFICATE OF CORRECTION

Page 1 of 2

PATENT NO. : 9,247,920 B2
APPLICATION NO. : 14/192466
DATED : February 2, 2016
INVENTOR(S) : Al Assad et al.

It is certified that error appears in the above-identified patent and that said Letters Patent is hereby corrected as shown below:

In the specification,

In Column 7, Line 6, delete "radiation 12" and insert -- radiation 20 --, therefor.

In Column 12, Line 10, delete "structure 96," and insert -- structure 86, --, therefor.

In Column 13, Line 19, delete "detector 22" and insert -- source 22 --, therefor.

In Column 16, Lines 29-30, delete "controller 148" and insert -- controller 48 --, therefor.

In Column 16, Line 67, delete "controller 148" and insert -- controller 48 --, therefor.

In Column 17, Line 6, delete "controller 148" and insert -- controller 48 --, therefor.

In Column 18, Line 58, delete "imager 32." and insert -- imager 30. --, therefor.

In Column 19, Line 57, delete "imager 30" and insert -- imager 32 --, therefor.

In Column 19, Line 60, delete "rotation 52" and insert -- rotation 42 --, therefor.

In Column 22, Line 25, delete "imager 30." and insert -- imager 32. --, therefor.

In Column 24, Line 11, delete "imager 30)," and insert -- imager 32), --, therefor.

In Column 24, Line 26, delete "feedback 96, 106" and insert -- feedback 98, 108 --, therefor.

In Column 24, Line 28, delete "imager 30" and insert -- imager 32 --, therefor.

In Column 26, Line 42, delete "rotation 24" and insert -- rotation 42 --, therefor.

Signed and Sealed this
Tenth Day of May, 2016

Michelle K. Lee
*Director of the United States Patent and Trademark Office*

CERTIFICATE OF CORRECTION (continued)
U.S. Pat. No. 9,247,920 B2

In Column 27, Lines 7-8, delete "imager 30" and insert -- imager 32 --, therefor.

In the claims,

In Column 30, Line 41, in Claim 21, delete "data" and insert -- data, --, therefor.